United States Patent
Kuriyama et al.

(10) Patent No.: US 9,890,359 B2
(45) Date of Patent: Feb. 13, 2018

(54) CULTURE MEDIUM FOR PROLIFERATING STEM CELL, WHICH CONTAINS SULFATED COMPOUND

(71) Applicant: AJINOMOTO CO., INC., Tokyo (JP)

(72) Inventors: Yoko Kuriyama, Kawasaki (JP); Nao Sugimoto, Kawasaki (JP); Manabu Kitazawa, Kawasaki (JP); Satoru Okamoto, Kawasaki (JP); Sho Senda, Kawasaki (JP); Ikue Harata, Kawasaki (JP); Satoru Ohashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 537 days.

(21) Appl. No.: 14/497,926

(22) Filed: Sep. 26, 2014

(65) Prior Publication Data
US 2015/0011003 A1    Jan. 8, 2015

Related U.S. Application Data

(63) Continuation of application No. PCT/JP2013/059745, filed on Mar. 29, 2013.

(30) Foreign Application Priority Data

Mar. 30, 2012  (JP) ................................ 2012-082205
Mar. 30, 2012  (JP) ................................ 2012-082609
Jan. 31, 2013  (JP) ................................ 2013-016505

(51) Int. Cl.
*C12N 5/0775*   (2010.01)
*C12N 5/074*    (2010.01)
*C08G 63/91*    (2006.01)
*C08G 65/48*    (2006.01)

(52) U.S. Cl.
CPC ......... *C12N 5/0663* (2013.01); *C08G 63/912* (2013.01); *C08G 65/48* (2013.01); *C12N 5/0696* (2013.01); *C12N 2500/34* (2013.01); *C12N 2501/115* (2013.01)

(58) Field of Classification Search
None
See application file for complete search history.

(56) References Cited

U.S. PATENT DOCUMENTS

| | | | |
|---|---|---|---|
| 5,122,597 A | | 6/1992 | Barritault et al. |
| 5,189,148 A | * | 2/1993 | Akiyama ............. A61K 9/5078 424/477 |
| 5,314,872 A | | 5/1994 | Kato et al. |
| 5,849,722 A | * | 12/1998 | Habuchi ............. A61K 31/715 435/101 |
| 2009/0148420 A1 | | 6/2009 | Cool et al. |

FOREIGN PATENT DOCUMENTS

| | | | | |
|---|---|---|---|---|
| EP | 0 345 660 A1 | | 12/1989 | |
| EP | 0 509 517 A2 | | 10/1992 | |
| GB | 1129133 A | | 10/1968 | |
| IT | WO 9213526 A1 | * | 8/1992 | ....... A61F 13/00063 |
| JP | EP 0345660 A1 | * | 12/1989 | .......... A61K 9/0019 |
| JP | 2-138223 A | | 5/1990 | |
| JP | 7-107970 A | | 4/1995 | |
| JP | 10-17498 A | | 1/1998 | |
| JP | 2000-1468 A | | 1/2000 | |
| WO | WO 92/13526 A1 | | 8/1992 | |
| WO | WO 95/09637 A1 | | 4/1995 | |
| WO | WO 2009/070842 A1 | | 6/2009 | |
| WO | WO 2011/108993 A1 | | 9/2011 | |
| WO | WO 2011/133902 A2 | | 10/2011 | |

OTHER PUBLICATIONS

Japanese Office Action issued Sep. 6, 2016 in Patent Application No. 2014-508234 (with English Translation).
International Search Report issued Jun. 11, 2013 in PCT/JP2013/059745.
International Preliminary Report on Patentability and Written Opinion dated Oct. 1, 2014 in PCT/JP2013/059745.
Michiru Ida et al., "Identification and Functions of Chondroitin Sulfate in the Milieu of Neural Stem Cells", J.Biol.Chem., Mar. 3, 2006, vol. 281, No. 9, pp. 5982-5991and Cover page.
Anna Calarco et al., "Controlled Delivery of the Heparan Sulfate/FGF-2 Complex by a Polyelectrolyte Scaffold Promotes Maximal hMSC Proliferation and Differentiation", J. Cell. Biochem., 2010, vol. 110, pp. 903-909.
D. Gospodarowicz et al., "Heparin Protects Basic and Acidic FGF From Inactivation", Journal of Cellular Physiology, vol. 128, 1986, pp. 475-484.
Extended Search Report dated Oct. 1, 2015 in European Patent Application No. 13768772.9.
Guokai Chen, et al., "Thermal Stability of Fibroblast Growth Factor Protein is a Determinant Factor in Regulating Self-Renewal, Differentiation, and Reprogramming in Human Pluripotent Stem Cells", Stem Cells, Embryonic Stem Cells/Induced Pluripotent Stem Cells, vol. 30, No. 4, 2012, XP055214916, pp. 623-630.
Mark E. Levenstein, et al., "Secreted Proteoglycans Directly Mediate Human Embryonic Stem Cell-Basic Fibroblast Growth Factor 2 Interactions Critical for Proliferation", Stem Cells, Embryonic Stem cells/Induced Pluripotent Stem Cells, vol. 26, No. 12, Dec. 2008, XP055214951, pp. 3099-3107.
Miho K. Furue, et al., "Heparin promotes the growth of human embryonic stem cells in a defined serum-free medium", PNAS, Proceedings of the National Academy of Science, Sep. 9, 2008, vol. 105, No. 36, XP55142731, 13 pages.
Nivedita Sangaj, et al."Heparin mimicking polymer promotes myogenic differentiation of muscle progenitor cells", Biomacromolecules, vol. 11, No. 12, Dec. 2010, XP055214469, pp. 3294-3300.
Michiya Matsusaki, et al., "Novel functional biodegradable polymer II: fibroblast growth factor-2 activities of poly(γ-glutamic acid)-sulfonate.", BIOMACROMOLECULES, Jan. 2005, vol. 6, No. 1, XP055215114, pp. 400-407.

(Continued)

*Primary Examiner* — Scott Long
*Assistant Examiner* — Nghi Nguyen
(74) *Attorney, Agent, or Firm* — Oblon, McClelland, Maier & Neustadt, L.L.P.

(57) ABSTRACT

A medium which comprises a fibroblast growth factor (FGF), and a sulfated compound or a pharmaceutically acceptable salt thereof at a concentration which promotes the growth of a stem cell in the presence of FGF, is useful for culturing stem cells.

11 Claims, No Drawings

(56) References Cited

OTHER PUBLICATIONS

Tomoko Kajio, et al., "Stabilization of basic fibroblast growth factor with dextran sulfate.", FEBS Letters, Jul. 1992 vol. 306, No. 2,3, XP000764982, pp. 243-246.

Singaporean Written Opinion dated Jul. 5, 2016 in Patent Application No. 11201406115V filed Mar. 29, 2013.

Thomas F. Zioncheck, et al., "Sulfated Oligosaccharides Promote Hepatocyte Growth Factor Association and Govern It's Mitogenic Activity" The Journal of Biological Chemistry, vol. 270, No. 28, Jul. 14, 1995, pp. 16871-16878.

Michiya Matsusaki, et al., "Novel Functional Biodegradable Polymer II: Fibroblast Growth Factor-2 Activities of Poly (gamma-glutamic acid)-sulfonate" Biomacromolecules, vol. 6, No. 1, Dec. 18, 2004, pp. 400-407.

Jens Dernedde, et al., "Dendritic polyalycerol sulfates as multivalent inhibitors of inflammation" PNAS, vol. 107, No. 46, Nov. 16, 2010, pp. 19679-19684.

Search Report dated Oct. 5, 2015 in Singaporean Patent Application No. 11201406115V.

Written Opinion dated Oct. 9, 2015 in Singaporean Patent Application No. 11201406115V.

Yuejie Zhang, et al., "Proliferative effects on neural stem/progenitor cells of a sulfated polysaccharide purified from the sea cucumber *Stichopus japonicus*.", Journal of Bioscience Bioengineering, 2010,109, No. 1, pp. 67-72.

Zeynep Oezyuerek, et al., "Sulfated glyco-block copolymers with specific receptor and growth factor binding to support cell adhesion and proliferation", Biomaterials, 2009, 30(6), pp. 1026-1035.

David B. Volkin, et al., "Sucralfate and soluble sucrose octasulfate bind and stabilize acidic fibroblast growth factor." Biochimica et Biophysica Acta, 1993,1203(1), pp. 18-26.

Brian K. Yeh, et al., "Structural basis for activation of fibroblast growth factor signaling by sucrose octasulfate." Molecular and Cellular Biology, 2002, vol. 22, No. 20, pp. 7184-92.

David M. Ornitz, et al., "FGF binding and FGF receptor activation by synthetic heparan-derived di- and trisaccharides." Science, 1995, vol. 268, (5209), pp. 432-436.

\* cited by examiner

CULTURE MEDIUM FOR PROLIFERATING STEM CELL, WHICH CONTAINS SULFATED COMPOUND

CROSS REFERENCES TO RELATED APPLICATIONS

This application is a continuation of International Patent Application No. PCT/JP2013/059745, filed on Mar. 29, 2013, and claims priority to Japanese Patent Application No. 2012-082205, filed on Mar. 30, 2012, Japanese. Patent Application No. 2012-082609, filed on Mar. 30, 2012, and Japanese Patent Application No. 2013-016505, filed on Jan. 31, 2013, all of which are incorporated herein by reference in their entireties.

BACKGROUND OF THE INVENTION

Field of the Invention

The present invention relates to a medium for stem cell proliferation containing a fibroblast growth factor, a culture method of stem cell using the medium, and the like.

DISCUSSION OF THE BACKGROUND

Background Art

Conventionally, the culture of stem cells (embryonic stem cell, artificial pluripotent stem cell and the like) has been performed using a medium containing a serum. For example, fetal bovine serum (FBS) and the like are widely used for cell culture as an important additive for cell proliferation. However, when stem cells after culture are used for medical purposes, a xeno-derived component may become a source of infection with blood-borne pathogen or a heterogeneous antigen. In addition, culture results may be inconsistent due to a difference between serum lots. Therefore, it has become mainstream in recent years to use a medium having a clear chemical composition (chemically-defined medium) for culturing stem cells, and the development of a serum-free medium is ongoing.

Fibroblast growth factor (FGF) is a protein having a molecular weight of 16,000 to 20,000, that promotes growth of fibroblasts and endothelial cells. FGF includes basic fibroblast growth factor (bFGF), acidic fibroblast growth factor (aFGF), keratinocyte growth factor (KGF) and the like, and not less than 20 kinds of FGF are respectively known for humans and mice. To stably perform stem cell culture, FGF is generally added to the medium, and is one of the highly important components for serum-free medium as well. However, FGF is expensive as compared to other components, and is known to show low stability in medium, which necessitates highly frequent medium exchange in the cell culture.

It has been reported heretofore that sulfated polysaccharides have an effect of protecting FGF from degradation, denaturation, deactivation and the like.

WO 1992/13526 discloses that carrageenan stabilizes bFGF. The examples of this document describe that a protecting agent containing sulfated polysaccharides such as heparin, dextran sulfate, carrageenan and the like protect a 5-fold amount (w/w) of bFGF (180 µg/200 µl) from hydrolysis caused by trypsin (Example 1) and denaturation due to heat (Example 3). It is also disclosed that protection from hydrolysis caused by trypsin requires the weight ratio of bFGF to be not more than 5 to 7 relative to the protector (Example 2).

JP-A-02-138223 discloses a stabilizing method of FGF or mutein thereof, including contacting FGF or mutein thereof and sulfated glucan in an aqueous medium, and the like. The examples of this document disclose that addition of sulfated glucan enables stable maintenance of FGF activity in an aqueous medium.

Also, J. Cell. Physiol., 1986, 128, 475-484 describes that heparin or hexuronyl hexosaminoglycan sulfate (HHS-4) protects bFGF from inactivation and potentiates its physiological activity. It also describes that such effect is found only when a high concentration of heparin (20 µg/ml) or HHS-4 (200 µg/ml) is contacted with the cells, wherein heparin shows suppressed cell proliferation seemingly ascribable to the toxicity at a high concentration (for example, not less than 10 µg/ml, depending on the concentration of bFGF).

WO 2009/070842 teaches that polysulfated polysaccharides such as dextran polysulfate, heparin and the like or biologically active molecular fragments thereof function to protect progenitor cells including multipotent cells, improve the survival rate thereof and control differentiation thereof, and discloses a composition containing a progenitor cell together with polysulfated polysaccharides or a biologically active molecular fragment thereof. The concentration of polysulfated polysaccharides in the composition is described to be within the range of 500 ng/ml to 10 mg/ml. While the composition is described to further contain FGF, the relationship between the above-mentioned functions of polysulfated polysaccharides and FGF is not disclosed at all.

WO 2011/108993 describes that carbohydrate-based macromolecules such as glucose polymer and the like act to promote the growth of human mesenchymal stem cells, and discloses that the effective concentration of a carbohydrate-based macromolecule is within the range of 2.5 mg/ml to 100 mg/ml.

However, it is not known at all whether or not a sulfate of macromolecular organic compounds other than polysaccharides in general has an effect of protecting FGF from degradation, denaturation, deactivation and the like, or influences cell growth in cell culture.

Thus, there remains a need for compounds and methods for protecting FGF from degradation, denaturation, deactivation and the like.

SUMMARY OF THE INVENTION

Accordingly, it is one object of the present invention to provide novel methods for promoting the growth of stem cells in a medium for stem cell proliferation containing FGF.

It is another object of the present invention to provide novel method of culturing stem cells, which uses a medium for stem cell proliferation containing FGF, and the like These and other objects, which will become apparent during the following detailed description, have been achieved by the inventors' discovery that a sulfated compound can act to suppress a decrease in the protein amount of FGF in a medium for stem cell proliferation, and promotes the growth of stem cell in the presence of FGF. The present inventors have studied in detail the concentration of a sulfated compound necessary for exhibiting a stem cell growth promoting effect in the presence of FGF, and unexpectedly noted a sulfated compound showing a remarkable stem cell growth promoting effect in the presence of FGF even when the compound was added to a medium at a concentration range showing a low suppressive effect on a decrease in the protein amount of FGF.

Accordingly, the present invention provides:

(1) A medium for stem cell proliferation, comprising a fibroblast growth factor (FGF), and a sulfated compound or a pharmaceutically acceptable salt thereof at a concentration promoting the growth of a stem cell in the presence of FGF (sulfated compound content is not more than 250 ng/ml when the sulfated compound is a sulfated polysaccharide).

(2) The medium of (1), wherein the sulfated compound is sulfated saccharide (the sulfated saccharide content is not more than 250 ng/ml when the sulfated saccharide is a sulfated polysaccharide).

(3) The medium of (2), wherein the aforementioned sulfated saccharide is at least one compound selected from the group consisting of:

(I) a compound comprising one or more constitutional units induced from a compound represented by the following formula (a):

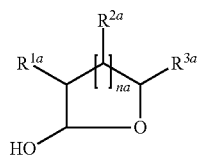

wherein
na is 1, 2 or 3,
$R^{1a}$ and $R^{3a}$ are the same or different and each is a functional group optionally having substituent(s), and
$R^{2a}$ in the number of na are each independently a functional group optionally having substituent(s), and one or more sulfate groups;

(II) a compound represented by the following formula (b):

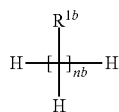

wherein
nb is an integer of 3 to 100, and
$R^{1b}$ in the number of nb are each independently a functional group optionally having substituent(s) and containing one or more sulfate groups; and (III) a compound represented by the following formula (c):

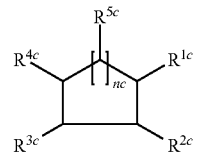

wherein
nc is 1, 2 or 3,
$R^{1c}$-$R^{4c}$ are the same or different and each is a functional group optionally having substituent(s), and
$R^{5c}$ in the number of nc are each independently a functional group optionally having substituent(s) and containing one or more sulfate groups.

(4) The medium of (2) or (3), wherein the sulfated saccharide is at least one selected from the group consisting of sulfated monosaccharide, sulfated disaccharide, sulfated polysaccharide, sulfated sugar alcohol and sulfated cyclitol.

(5) The medium of any of (2)-(4), wherein the content level of sulfur in the sulfated saccharide is not less than 5 wt %.

(6) The medium of any of (2)-(5), wherein the aforementioned sulfated saccharide or a pharmaceutically acceptable salt thereof is at least one selected from the group consisting of dextran sulfate Na, cellulose $SO_3Na$, xanthan gum $SO_3Na$, pectin $SO_3Na$, fucoidan, alginate $SO_3Na$, inulin $SO_3Na$, maltoheptaose $SO_3Na$, stachyose $SO_3Na$, maltotriose $SO_3Na$, maltitol $SO_3Na$, sucrose $8SO_3K$, glucose $SO_3Na$, myo-6 inositol $SO_3K$, α-cyclodextrin $SO_3Na$, mannitol $SO_3Na$, xylitol $SO_3Na$ and erythritol $SO_3Na$.

(7) The medium of (6), wherein the aforementioned sulfated saccharide or a pharmaceutically acceptable salt thereof is at least one selected from the group consisting of dextran sulfate Na, fucoidan, xanthan gum $SO_3Na$, pectin $SO_3Na$, maltoheptaose $SO_3Na$, maltotriose $SO_3Na$, maltitol $SO_3Na$ and sucrose $8SO_3K$.

(8) The medium of any of (2)-(7), wherein the aforementioned sulfated saccharide or a pharmaceutically acceptable salt thereof is dextran sulfate Na having an average molecular weight of 2,500 to 7,500.

(9) The medium of any of (2)-(7), wherein the aforementioned sulfated saccharide or a pharmaceutically acceptable salt thereof is sucrose $8SO_3K$.

(10) The medium of (9), wherein the content of the aforementioned sucrose $8SO_3K$ is 25 pg/ml to 10 μg/ml.

(11) The medium of (1), wherein the sulfated compound is a sulfated polymer (excluding sulfated saccharides).

(12) The medium of (11), wherein the aforementioned sulfated polymer is a compound represented by the following formula (I):

wherein
A is a polymer constitutional unit,
n is an integer of 1 to 1500,
$R^1$ is a functional group optionally having substituent(s), which contains one or more sulfo groups.

(13) The medium of (11) or (12), wherein the content level of sulfur in the sulfated polymer is not less than 5 wt %.

(14) The medium of any of (11)-(13), wherein the sulfated polymer is at least one selected from the group consisting of sulfo group-containing polyvinyl alcohol, sulfo group-containing polyvinyl amine, sulfo group-containing polyallylamine, sulfo group-containing polyethyleneimine, sulfo group-containing α-polylysine, sulfo group-containing α-poly methyl glutamate/α-5-hydroxynorvaline (2/8) copolymer, α-polyglutamic acid-γ-taurine, sulfo group-containing triserine, sulfo group-containing serine, sulfo group-containing branched-polyglycerol and a derivative thereof, and polyethylene sulfonate.

(15) The medium of (14), wherein the derivative of sulfo group-containing branched-polyglycerol or a pharmaceutically acceptable salt thereof is branched-polyglycerol-monomethyltetraethyleneglycol-$SO_3Na$, branched-polyglycerol-2-furfuryl-$SO_3Na$ or branched-polyglycerol-isopropyloxy-$SO_3Na$.

(16) The medium of (1), wherein the sulfated compound is a sulfated substance of a saccharide polymer crosslinked by a diisocyanate compound.

(17) The medium of (16), wherein the sulfated substance of a saccharide polymer crosslinked by a diisocyanate compound or a pharmaceutically acceptable salt thereof is maltotriose-hexamethylene diisocyanate-SO₃Na or dextran-hexamethylene diisocyanate-SO₃Na.

(18) The medium of (1), wherein the sulfated compound is a sulfated substance of sugar-lactone.

(19) The medium of (18), wherein the sulfated substance of sugar-lactone or a pharmaceutically acceptable salt thereof is gluconolactone-SO₃Na.

(20) The medium of (1) wherein the sulfated compound is a sulfated substance of an organic acid.

(21) The medium of (20), wherein the sulfated substance of an organic acid or a pharmaceutically acceptable salt thereof is tartrate-SO₃Na.

(22) The medium of any of (1)-(21), wherein the fibroblast growth factor is a basic fibroblast growth factor.

(23) The medium of any of (1)-(22), wherein the aforementioned stem cell is a mesenchymal stem cell, an embryonic stem cell or an artificial pluripotent stem cell.

(24) A culture method of a stem cell using a medium for stem cell proliferation comprising FGF, comprising adding a sulfated compound or a pharmaceutically acceptable salt thereof to the medium at a concentration promoting the growth of a stem cell in the presence of FGF (sulfated compound content is not more than 250 ng/ml when the sulfated compound is a sulfated polysaccharide).

(25) The method of (24), wherein the sulfated compound is a sulfated saccharide (sulfated saccharide content is not more than 250 ng/ml when the sulfated saccharide is a sulfated polysaccharide).

(26) The method of (25), wherein the aforementioned sulfated saccharide is at least one compound selected from the group consisting of:

(I) a compound comprising one or more constitutional units induced from a compound represented by the following formula (a):

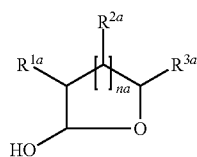

wherein
na is 1, 2 or 3,
$R^{1a}$ and $R^{3a}$ are the same or different and each is a functional group optionally having substituent(s), and
$R^{2a}$ in the number of na are each independently a functional group optionally having substituent(s), and one or more sulfate groups;

(II) a compound represented by the following formula (b):

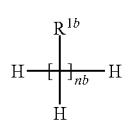

wherein
nb is an integer of 3 to 100, and
$R^{1b}$ in the number of nb are each independently a functional group optionally having substituent(s) and containing one or more sulfate groups; and (III) a compound represented by the following formula (c):

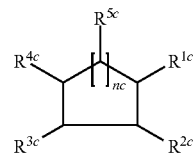

wherein
nc is 1, 2 or 3,
$R^{1c}$-$R^{4c}$ are the same or different and each is a functional group optionally having substituent(s), and
$R^{5c}$ in the number of nc are each independently a functional group optionally having substituent(s) and containing one or more sulfate groups.

(27) The method of (25) or (26), wherein the sulfated saccharide is at least one selected from the group consisting of sulfated monosaccharide, sulfated disaccharide, sulfated polysaccharide, sulfated sugar alcohol and sulfated cyclitol.

(28) The method of any of (25)-(27), wherein the content level of sulfur in the sulfated saccharide is not less than 5 wt %.

(29) The method of any of (25)-(28), wherein the aforementioned sulfated saccharide or a pharmaceutically acceptable salt thereof is at least one selected from the group consisting of dextran sulfate Na, cellulose SO₃Na, xanthan gum SO₃Na, pectin SO₃Na, fucoidan, alginate SO₃Na, inulin SO₃Na, maltoheptaose SO₃Na, stachyose SO₃Na, maltotriose SO₃Na, maltitol SO₃Na, sucrose 8SO₃K, glucose SO₃Na, myo-6 inositol SO₃K, α-cyclodextrin SO₃Na, mannitol SO₃Na, xylitol SO₃Na and erythritol SO₃Na.

(30) The method of (29), wherein the aforementioned sulfated saccharide or a pharmaceutically acceptable salt thereof is at least one selected from the group consisting of dextran sulfate Na, fucoidan, xanthan gum SO₃Na, pectin SO₃Na, maltoheptaose SO₃Na, maltotriose SO₃Na, maltitol SO₃Na and sucrose 8SO₃K.

(31) The method of any of (25)-(30), wherein the aforementioned sulfated saccharide or a pharmaceutically acceptable salt thereof is dextran sulfate Na having an average molecular weight of 2,500 to 7,500.

(32) The method of any of (25)-(30), wherein the aforementioned sulfated saccharide or a pharmaceutically acceptable salt thereof is sucrose 8SO₃K.

(33) The method of (32), wherein the content of the aforementioned sucrose 8SO₃K is 25 pg/ml to 10 μg/ml.

(34) The method of (24), wherein the sulfated compound is a sulfated polymer (excluding sulfated saccharides).

(35) The method of (34), wherein the aforementioned sulfated polymer is a compound represented by the following formula (I):

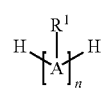

wherein
A is a polymer constitutional unit,
n is an integer of 1 to 1500,
$R^1$ is a functional group optionally having substituent(s), which contains one or more sulfo groups.

(36) The method of (34) or (35), wherein the content level of sulfur in the sulfated polymer is not less than 5 wt %.

(37) The method of any of (34)-(36), wherein the sulfated polymer is at least one selected from the group consisting of sulfo group-containing polyvinyl alcohol, sulfo group-containing polyvinyl amine, sulfo group-containing polyallylamine, sulfo group-containing polyethyleneimine, sulfo group-containing α-polylysine, sulfo group-containing α-poly methyl glutamate/α-5-hydroxynorvaline (2/8) copolymer, α-polyglutamic acid-γ-taurine, sulfo group-containing triserine, sulfo group-containing serine, sulfo group-containing branched-polyglycerol and a derivative thereof, and polyethylene sulfonic acid.

(38) The method of the above-mentioned (37), wherein the derivative of the sulfo group-containing branched-polyglycerol or a pharmaceutically acceptable salt thereof is branched-polyglycerol-monomethyltetraethyleneglycol-SO₃Na, branched-polyglycerol-2-furfuryl-SO₃Na or branched-polyglycerol-isopropyloxy-SO₃Na.

(39) The method of (24), wherein the sulfated compound is a sulfated substance of a saccharide polymer crosslinked by a diisocyanate compound.

(40) The method of (39), wherein the sulfated substance of a saccharide polymer crosslinked by a diisocyanate compound or a pharmaceutically acceptable salt thereof is maltotriose-hexamethylene diisocyanate-SO₃Na or dextran-hexamethylene diisocyanate-SO₃Na.

(41) The method of (24), wherein the sulfated compound is a sulfated substance of sugar-lactone.

(42) The method of (41), wherein the sulfated substance of sugar-lactone or a pharmaceutically acceptable salt thereof is gluconolactone-SO₃Na.

(43) The method of (24), wherein the sulfated compound is a sulfated substance of an organic acid.

(44) The method of (43), wherein the sulfated substance of an organic acid or a pharmaceutically acceptable salt thereof is tartrate-SO₃Na.

(45) The method of any of (24)-(44), wherein the fibroblast growth factor is a basic fibroblast growth factor.

(46) The method of any of (24)-(45), wherein the aforementioned stem cell is a mesenchymal stem cell, an embryonic stem cell or an artificial pluripotent stem cell.

(47) A sulfated compound selected from the group consisting of xylitol SO₃Na, maltotriose-hexamethylene diisocyanate-SO₃Na and gluconolactone-SO₃Na or a pharmaceutically acceptable salt thereof.

(48) A sulfated compound selected from the group consisting of an α-poly methyl glutamate/α-5-hydroxynorvaline (5-SO₃Na) (2/8) copolymer, triserine-SO₃Na and branched-polyglycerol-isopropyloxy-SO₃Na or a pharmaceutically acceptable salt thereof.

Using the medium of the present invention, a stem cell can be efficiently grown. Consequently, the frequency of medium exchange during culture can be reduced, and the cost of stem cell culture can be decreased.

DETAILED DESCRIPTION OF THE PREFERRED EMBODIMENTS

The present invention provides a medium for stem cell proliferation comprising a fibroblast growth factor, and a sulfated compound or a pharmaceutically acceptable salt thereof at a concentration promoting the growth of a stem cell in the presence of FGF (hereinafter to be also referred to as the medium of the present invention).

In the present invention, the term sulfated compound refers to a sulfated substance of any compound, which can promote the growth of a stem cell in the presence of FGF.

In the present invention, a sulfated compound or a pharmaceutically acceptable salt thereof "promotes the growth of a stem cell in the presence of FGF" means that a cell number of generally not less than 100%, preferably not less than 120%, is obtained when a sulfated compound or a pharmaceutically acceptable salt thereof is contained in the medium, wherein the cell number of the stem cells cultured under the same conditions except that a sulfated compound or a pharmaceutically acceptable salt thereof is not contained and in the presence of FGF is the standard (100%). FGF only needs to be present at the below-mentioned concentration capable of promoting the growth of a stem cell. Whether the growth of a stem cell is promoted in the presence of FGF can be evaluated by a method using a known cell proliferation system, such as the method described in the Examples and the like.

A sulfated compound in the present invention is preferably a sulfated saccharide, a sulfated polymer, a sulfated substance of a saccharide polymer crosslinked by a diisocyanate compound, a sulfated substance of sugar lactone or a sulfated substance of an organic acid.

In one embodiment of the present invention, the sulfated compound is a sulfated saccharide. In the present invention, the sulfated saccharide is a sulfated substance of a saccharide. The "saccharide" is not particularly limited as long as it is known in the technical field, or may be novel. The saccharide may be a natural product or synthesized product. The sulfated saccharides to be added to the medium of the present invention preferably include sulfated monosaccharide, sulfated disaccharide, sulfated polysaccharide, sulfated sugar alcohol and sulfated cyclitol.

One embodiment of the sulfated saccharide is (I) a compound comprising one or more constitutional units induced from a compound represented by the following formula (a):

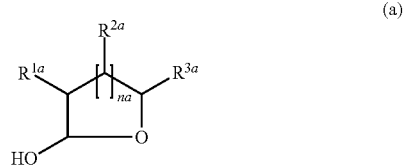

(a)

wherein
na is 1, 2 or 3,
$R^{1a}$ and $R^{3a}$ are the same or different and each is a functional group optionally having substituent(s), and
$R^{2a}$ in the number of na are each independently a functional group optionally having substituent(s), and one or more sulfate groups (hereinafter sulfated saccharide I).

The "constitutional units induced from a compound represented by the following formula (a)" here is a unit induced from a monomer compound represented by the formula (a) and contained in sulfated saccharide I (hereinafter to be also referred to as constitutional unit a, for convenience).

In the present specification, the "functional group" means an atom or atomic group present in a molecule of an organic compound and causing the reactivity characteristic of the compound. Specifically, it is constituted by hydrogen, carbon, nitrogen, oxygen and the like.

Examples of the functional group include hydroxyl group, alkoxy group, amino group, acylamino group, carboxyl group, ester group, amide group, formyl group, carbonyl group, hydroxyalkyl group, alkyl group (e.g., straight chain or branched alkyl groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like, cyclic alkyl groups such as cyclopropyl, cyclobutyl, cyclopentyl, cyclohexyl, cycloheptyl and the like, aliphatic heterocycles such as pyrrolidine, tetrahydrofuran, tetrahydrothiophene and the like, and the like), aryl group (e.g., groups such as phenyl, naphthyl, pyridyl, pyrimidyl, pyrazinyl, triazinyl, indolizyl, imidazolyl, thiazolyl, oxazolyl, purinyl, quinolinyl and the like) and the like.

While the "substituent" of the "functional group optionally having substituent(s)" is not particularly limited as long as it is generally utilized for constituting a saccharide, examples thereof include hydroxyl group, amino group, carboxyl group, formyl group, carbonyl group and the like. These functional groups are optionally further substituted by sulfate group, phosphate group, acetyl group, amide group and the like. When two or more substituents are present, they may be the same or different.

Preferable examples of the functional group constituting $R^{1a}$-$R^{3a}$ include hydroxyl group, alkoxy group, amino group, acylamino group, carboxyl group, hydroxyalkyl group, and alkyl group (e.g., methyl). As the substituent that the functional group optionally has, hydroxyl group is preferable.

In addition, —OH in the constitutional unit represented by the formula (a), when it is not involved in the linking of constitutional units and it is present at the terminal of a sulfated saccharide, optionally has substituent(s). Examples of the substituent include sulfate group, phosphate group, acetyl group, amide group and the like.

When sulfated saccharide I is a compound containing two or more constitutional units a, the respective constitutional units may be the same or different. While the constitutional units may be linked via a spacer (linking group), they are preferably linked by a glycosidic bond without via a spacer. The glycosidic bond may be an α type or a β type. The manner of glycosidic bond is not particularly limited, and may be any of α-1,2 bond, β-1,2 bond, α-1,3 bond, β-1,3 bond, α-1,4 bond, β-1,4 bond, α-1,5 bond, β-1,5 bond, α-1,6 bond, β-1,6 bond, and the like can be mentioned. It may be any of these, or plural binding manners may be contained in one molecule.

The number of constitutional units a in a sulfated saccharide I, which is preferable for the proliferation of mesenchymal stem cells is generally 1 to 5,000, preferably 1 to 500, more preferably 1 to 50, most preferably 1 to 30. The number of constitutional units a in a sulfated saccharide I, which is preferable for the proliferation of pluripotent stem cells is generally 1 to 100,000, preferably 1 to 10,000, more preferably 1 to 5,000, most preferably 1 to 1,000.

The sulfated saccharide I contains one or more sulfate groups. The sulfated saccharide I as a whole only needs to contain one or more sulfate groups, each constitutional unit does not need to contain a sulfate group. The sulfate group is a sulfate group in $R^{1a}$-$R^{3a}$ in the constitutional unit a, or a sulfate group as a substituent of —OH in the constitutional unit a, is generally introduced by sulfation of any functional group capable of sulfation such as hydroxyl group and the like, and the position thereof is not particularly limited. While the number of sulfate group in sulfated saccharide I can vary depending on the number of constitutional units, the number of functional groups capable of sulfation and the like, it is preferably about 1.5 residues/constitutional unit a.

A compound containing one constitutional unit a and one or more sulfate groups corresponds to a sulfated monosaccharide.

As the monosaccharide, one known in the technical field can be employed without any particular limitation, and it may be a novel monosaccharide. The number of carbons constituting carbohydrate is not limited and may be any of, for example, tetrose, pentose, hexose, heptose and the like. Specific examples of the monosaccharide include glucose, galactose, mannose, talose, idose, altrose, allose, gulose, xylose, arabinose, rhamnose, fucose, fructose, ribose, deoxyribose, glucosamine, galactosamine, glucuronic acid, galacturonic acid and the like. The sulfated monosaccharide is a sulfated substance of these monosaccharides, preferably sulfated substance of glucose (e.g., glucose $SO_3H$ etc.).

A compound containing two or more constitutional units a and one or more sulfate groups corresponds to sulfated disaccharide or sulfated polysaccharide.

Disaccharide is a carbohydrate wherein two molecules of the aforementioned monosaccharide are bonded by a glycosidic bond to become one molecule, and one known in the technical field can be employed without any particular limitation, which may be a novel disaccharide. The manner of glycosidic bond is not particularly limited, and may be any of α-1,2 bond, β-1,2 bond, α-1,3 bond, β-1,3 bond, α-1,4 bond, β-1,4 bond, α-1,5 bond, β-1,5 bond, α-1,6 bond, β-1,6 bond, α-1, α-1 bond, α-1, β-1 bond, α-1, β-2 bond and the like. Specific examples of the disaccharide include sucrose, lactose, maltose, trehalose, cellobiose, maltitol and the like. The sulfated disaccharide is a sulfated substance of these disaccharides, preferably a sulfated substance of sucrose (e.g., sucrose $8SO_3H$ etc.) and a sulfated substance of maltitol (e.g., maltitol $SO_3H$ etc.).

The polysaccharide is a carbohydrate wherein three or more molecules of the aforementioned monosaccharide are bonded by a glycosidic bond to become one molecule, and one known in the technical field can be employed without any particular limitation, which may be a novel polysaccharide. Polysaccharide may consist of only one kind of the aforementioned saccharides, or two or more kinds thereof may be combined. Polysaccharide may be any of linear, branched and cyclic.

Examples of the polysaccharide include amylose, amylopectin, glycogen, dextrin, α-cyclodextrin, β-cyclodextrin, γ-cyclodextrin, dextran, pullulan, cellulose and a derivative thereof (e.g., hydroxyethyl cellulose, hydroxypropyl cellulose etc.), laminaran, curdlan, callose, mannan, glucomannan, galactomannan, xylan, glucuronoxylan, arabinoxylan, araban, galactan, galacturonan, chitin, chitosan, xyloglucan, pectic acid and pectin, alginic acid, arabinogalactan, glycosaminoglycan (e.g., heparin, heparan sulfate, hyaluronic acid, chondroitin 4-sulfate, chondroitin 6-sulfate, dermatan sulfate, keratan sulfate etc.), guar gum, xanthan gum, fucoidan, inulin and the like, with preference given to dextran, cellulose, xanthan gum, fucoidan, alginic acid, inulin, α-cyclodextrin, maltoheptaose, stachyose and maltotriose. The sulfated polysaccharide is sulfated substance of these polysaccharides. Among the above-mentioned saccharides, those already sulfated (e.g., heparin, heparan sulfate, chondroitin 4-sulfate, chondroitin 6-sulfate, dermatan sulfate, keratan sulfate, fucoidan etc.) include the saccharides themselves. As the sulfated polysaccharide, dextran sulfate, sulfated substance of cellulose (i.e., cellulose $SO_3H$), sulfated substance of xanthan gum (i.e., xanthan gum $SO_3H$), fucoidan, sulfated substance of alginic acid (i.e., alginate $SO_3H$), sulfated substance of inulin (i.e., inulin $SO_3H$), sulfated substance of α-cyclodextrin (i.e., α-cyclodextrin $SO_3H$), sulfated substance of maltoheptaose (i.e., maltoheptaose $SO_3H$), sulfated substance of stachyose (i.e., stachyose $SO_3H$) and sulfated substance of maltotriose (i.e., maltotriose $SO_3H$) are preferable.

Another embodiment of the sulfated saccharide is (II) a compound represented by the following formula (b):

wherein
nb is an integer of 3 to 100, and
$R^{1b}$ in the number of nb are each independently a functional group optionally having substituent(s) and containing one or more sulfate groups (hereinafter sulfated saccharide II).

As the functional group and the substituent that the functional group optionally has, those similar to the aforementioned can be recited. The functional group constituting $R^{1b}$ is preferably a hydroxyl group.

The sulfated saccharide II contains one or more sulfate groups. The sulfate group is a sulfate group in $R^{1b}$ in the above-mentioned formula (b), is generally introduced by sulfation of any functional group capable of sulfation such as hydroxyl group and the like, and the position thereof is not particularly limited. While the number of sulfate group in sulfated saccharide II can vary depending on the number of functional groups capable of sulfation and the like, it is preferably about 1.5 residues/sulfated saccharide II.

Sulfated saccharide II corresponds to sulfated sugar alcohol.

The sugar alcohol is a compound produced by reducing the carbonyl group of the aforementioned monosaccharide. One known in the technical field can be employed without any particular limitation, and it may be a novel sugar alcohol. Examples of the sugar alcohol include glycerol, erythritol, threitol, arabinitol, xylitol, sorbitol, mannitol, volemitol, perseitol and the like, and erythritol, xylitol and mannitol are preferable. The sulfated sugar alcohol is a sulfated substance of these sugar alcohols, and a sulfated substance of glycerol (i.e., glycerol $SO_3H$), a sulfated substance of erythritol (i.e., erythritol $SO_3H$), a sulfated substance of xylitol (i.e., xylitol $SO_3H$) and a sulfated substance of mannitol (i.e., mannitol $SO_3H$) are preferable.

Another embodiment of the sulfated saccharide is (III) a compound represented by the following formula (c):

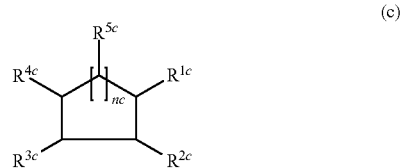

wherein
nc is 1, 2 or 3,
$R^{1c}$-$R^{4c}$ are the same or different and each is a functional group optionally having substituent(s), and
$R^{5c}$ in the number of nc are each independently a functional group optionally having substituent(s) and containing one or more sulfate groups (hereinafter sulfated saccharide III).

As the functional group and the substituent that the functional group optionally has, those similar to the aforementioned can be recited. The functional group constituting $R^{1c}$-$R^{5c}$ is preferably a hydroxyl group.

The sulfated saccharide III contains one or more sulfate groups. The sulfate group is a sulfate group in one or more of $R^{1c}$-$R^{5c}$ in the above-mentioned formula (c), is generally introduced by sulfation of any functional group capable of sulfation such as hydroxyl group and the like, and the position thereof is not particularly limited. While the number of sulfate group in sulfated saccharide III can vary depending on the number of functional groups capable of sulfation and the like, it is preferably about 1.5 residues/sulfated saccharide III.

Sulfated saccharide III corresponds to sulfated cyclitol.

The cyclitol is polyhydroxycycloalkane, and also called cyclic sugar alcohol or cyclit. As cyclitol, one known in the technical field can be employed without any particular limitation, and it may be a novel cyclitol. While cyclitol is known to include many isomers, any isomer may be used. While the number of carbons constituting the ring is not particularly limited, a 6-membered ring is preferable. Examples of the cyclitol include inositol (1,2,3,4,5,6-cyclohexanehexaol), a derivative of inositol (derivative wherein hydroxy group is substituted by amino group, ketone group, carboxyl group etc.) and the like, and inositol (e.g., myo-inositol etc.) are preferable. The sulfated cyclitol is a sulfated substance of these cyclitols, and a sulfated substance of inositol (e.g., myo-inositol $6SO_3H$) is preferable.

The content level of sulfur in the sulfated saccharide is generally not less than 5 wt %, preferably not less than 10 wt %, more preferably not less than 15 wt %, and the upper limit is generally not more than 40 wt %, preferably not more than 35 wt %, more preferably not more than 30 wt %. When it is within this range, it can promote the growth of stem cell in the presence of FGF. Here, the content level of sulfur is a proportion in wt % of sulfur derived only from the sulfate group in sulfated saccharides, which can be measured by a method known in the field (e.g., rhodizonate method, elemental analysis or luminescent spectral analysis). For example, the sulfur content of sucrose $8SO_3K$ used in the below-mentioned Examples is 19.5 wt % (48.8 wt % in sulfate group content level), and the sulfur content of dextran sulfate Na is 19.15 wt % (47.9 wt % in sulfate group content level).

Sulfated saccharides also encompass optical isomers, stereoisomers, tautomers, rotamers, and mixtures thereof at an optional ratio. These can be each obtained as a single product by synthesis methods and separation methods known per se. For example, an optical isomer can be obtained by using an optically active synthesis intermediate or by optical resolution of a synthesis intermediate or a racemate of the final product by a conventional method.

Sulfated saccharides further encompass stable isotopes and radioactive isotopes.

The sulfated saccharides to be contained in the medium of the present invention may be in the form of a pharmaceutically acceptable salt. Examples of such salt include salts of a sulfate group etc. present in the sulfated saccharides and a base. Specific examples thereof include alkali metal salts such as sodium salt, potassium salt and the like; alkaline earth metal salts such as calcium salt, magnesium salt and the like; salts with inorganic base such as aluminum salt, ammonium salt and the like; salts with organic base such as trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like, which can be prepared from a free form by a conventional method. As the pharmaceutically acceptable salt of the sulfated saccharides, a sodium salt or potassium salt of a sulfate group is preferable. Examples thereof include sucrose $8SO_3K$, dextran sulfate Na (molecular weight 5,000, 25,000, 500,000 etc.), cellulose $SO_3Na$, xanthan gum $SO_3Na$, alginate $SO_3Na$, inulin $SO_3Na$, α-cyclodextrin $SO_3Na$, erythritol $SO_3Na$, xylitol $SO_3Na$, mannitol $SO_3Na$, myo-inositol $6SO_3K$ and the like Xylitol $SO_3Na$ is a novel compound.

The average molecular weight of sulfated saccharides or a pharmaceutically acceptable salt thereof is not particularly limited, and varies depending on the kind of the sulfated saccharides to be employed and the kind of the salt. For the proliferation of mesenchymal stem cells, it is generally 50 to 1,000,000, preferably 100 to 700,000, more preferably 300 to 500,000, most preferably 500 to 100,000. For the proliferation of pluripotent stem cells, it is generally 50 to 50,000,000, preferably 100 to 5,000,000, more preferably 300 to 2,500,000, most preferably 500 to 500,000. When the average molecular weight is too large (for example, over 1,000,000 in mesenchymal stem cell proliferation), addition thereof at a concentration not less than a given level tends to cause toxicity or suppression of cell proliferation seemingly due to the inhibition of cell adhesion and the like. The average molecular weight can be measured by gel permeation chromatography and the like.

For example, the average molecular weight of the dextran sulfate Na is generally 1000 to 700,000, preferably 1000 to 300,000, more preferably 1000 to 100,000, most preferably 2,500 to 7,500.

In one embodiment of the present invention, the sulfated compound is a sulfated polymer. In the present invention, the sulfated polymer is a sulfated substance of any polymer. As long as the polymer is a compound produced by polymerization of plural monomers, it may be known in the technical field, or novel, or may be a naturally occurring substance or a synthesized product.

In the present invention, the sulfated saccharides are not included in sulfated polymer.

Examples of the kind of the polymer include polyester, polyvinyl, polyamide, polyamine, polyether, polycarbonate, polyalkyl, polyaryl, polyimide, polyurethane, epoxy resin and the like, and a polymer composed of a combination of these is also included in the polymer in the present invention.

The polymer may have any form such as straight chain polymer, branched-polymer (e.g., comb polymer, star-shaped polymer, dendrimer etc.), crosslinked polymer and the like.

The polymer may be produced by polymerization of one kind of monomers, or may be a copolymer. When it is a copolymer, the arrangement of the monomers to be polymerized, the presence or absence of branch and the like are not particularly limited, and the copolymer may be any of random copolymer, block copolymer, graft copolymer and the like.

While the polymer to be used in the present invention varies depending on the kind of the monomers constituting the polymer, it is a polymer of generally about 1 to 1500, preferably about 3 to 1000 monomers, and has a molecular weight of about 200 to 400,000, preferably about 500 to 100,000.

The sulfated polymer contains one or more "functional groups optionally having substituent(s)". In the present specification, the "functional group" means an atom or atomic group present in a molecule of an organic compound and causing the reactivity characteristic of the compound. Specifically, it is constituted by hydrogen, carbon, nitrogen, oxygen and the like.

Examples of the functional group include a functional group constituted by hydrogen, carbon, nitrogen, oxygen and the like, for example, hydroxyl group, alkoxy group, amino group, acylamino group, carboxyl group, ester group, amide group, formyl group, carbonyl group, hydroxyalkyl group, alkyl group (e.g., straight chain or branched alkyl groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like, cyclic alkyl groups such as cyclopropyl, cyclobutyl, cyclopentyl, cyclohexyl, cycloheptyl and the like, and the like), aliphatic heterocycles such as pyrrolidine, tetrahydrofuran, tetrahydrothiophene and the like, and the like, aryl or heteroaryl group (e.g., groups such as phenyl, naphthyl, pyridinyl, pyrimidyl, pyrazinyl, triazinyl, indolizyl, imidazolyl, thiazolyl, oxazolyl, purinyl, quinolinyl and the like) and the like. The functional group is preferably hydroxyl group, amino group or alkyl group, since sulfate group is easily introduced. When two or more functional groups are present, they may be the same or different.

While the "substituent" of the "functional group optionally having substituent(s)" is not particularly limited as long as it is generally utilized for constituting a polymer, examples thereof include sulfo group, phosphate group, acyl group, amide group and the like. When two or more substituents are present, they may be the same or different.

The sulfated polymer can be obtained by introducing one or more sulfo groups into the above-mentioned polymer. The monomers constituting the sulfated polymer does not need to each contain a sulfo group. The sulfo group is a functional group in the monomer constituting the sulfated polymer, includes one introduced by sulfation of optional functional group capable of sulfation such as hydroxyl group, amino group and the like in the monomer, and the position thereof is not particularly limited. Also, the number of the sulfo groups in the sulfated polymer is not particularly limited, and it can vary depending on the number of the monomers to be polymerized (degree of polymerization), the number of the functional groups capable of sulfation and the like.

The method of introducing a sulfo group into the polymer is not particularly limited. It is possible to obtain a sulfated polymer by polymerization of monomers introduced with a sulfo group in advance, or obtain a sulfated polymer by polymerizing monomers to give a polymer, and sulfation the obtained polymer. Sulfation can be performed according to a method known in the field.

One embodiment of the sulfated polymer is a compound represented by the following formula (I):

(I)

wherein

A is a polymer constitutional unit, n is an integer of 1 to 1500, $R^1$ is a functional group optionally having substituent(s), which contains one or more sulfo groups.

A in the number of n may be the same (polymer) or different (copolymer), and the binding (polymerization) manner thereof is not particularly limited and may be any of straight chain, branched (e.g., comb-shaped, star-shaped, dendritic etc.), crosslinked type and the like. When it is a copolymer, the arrangement of the monomers to be polymerized, the presence or absence of branch and the like are not particularly limited, and the copolymer may be any of random copolymer, block copolymer, graft copolymer and the like.

While n means the number of constitutional units A in a sulfated polymer, namely, the degree of polymerization, n is 1 to 1500, preferably 3 to 1000, more preferably 3 to 700, in the present invention.

A in the formula (I) is not particularly limited as to its structure as long as it is a polymer constitutional unit. For example, it is derived from a hydrocarbon (aliphatic hydrocarbon, aromatic hydrocarbon) and may contain oxygen, nitrogen and the like. Examples of the aliphatic hydrocarbon include saturated aliphatic hydrocarbon (e.g., ethane, 2-methylbutane, pentane, 2,2-dimethylbutane, 2,3-dimethylbutane, hexane, 2-methylpentane, 3-methylpentane, 2,2-dimethylpentane, 2,3-dimethylpentane, 2,4-dimethylpentane, 3,3-dimethylpentane, heptane, 2-methylhexane, 3-methylhexane, 2,2,3-trimethylbutane, 2,2-dimethylhexane, 2,5-dimethylhexane, 3,4-dimethylhexane, hexamethylethane, 2-methylheptane, 4-methylheptane, octane, 2,2,4-trimethylpentane, 2,3,4-trimethylpentane, nonane, decane, undecane, dodecane, tridecane, tetradecane, 1-pentadecane) and unsaturated aliphatic hydrocarbon (e.g., alkenes such as ethylene, propylene, butene, pentene and the like, alkynes such as acetylene, methylacetylene and the like, alkadienes such as butadiene, pentadiene and the like, cycloalkenes such as cyclopentene, cyclohexene and the like). Examples of the aromatic hydrocarbon include benzene, toluene, xylene, inden, naphthalene, phenanthrene and the like.

Specific examples of the polymer constitutional unit include constitutional units such as polyester, polyvinyl, polyamide, polyamine, polyether, polycarbonate, polyaryl, polyimide, polyurethane, epoxy resin and the like.

In the formula (I), $R^1$ is a functional group optionally having substituent(s). The "functional group optionally having substituent(s)" is similar to those mentioned above. Preferable examples of the functional group constituting $R^1$ include alkyl group (e.g., methyl), carbonyl group, hydroxyl group, alkoxyl group, amino group, acylamino group, hydroxyalkyl group, and aryl group (e.g., phenyl). As the substituent that the functional group optionally has, sulfo group is preferable.

The content level of sulfur in the sulfated polymer is generally not less than 5 wt %, preferably not less than 10 wt %, more preferably not less than 15 wt %, and the upper limit is generally not more than 40 wt %. When it is within this range, it can promote the growth of stem cell in the presence of FGF. Here, the content level of sulfur is a proportion in wt % of sulfur in the sulfated polymer, which can be measured by a method known in the field such as rhodizonate method, elemental analysis or luminescent spectral analysis). For example, the content level of sulfur of polyallylamine $SO_3Na$ used in the below-mentioned Examples is 19.43 wt % (48.6 wt % in sulfo group content level).

The sulfated polymer also encompasses optical isomers, stereoisomers, tautomers, rotamers, and mixtures thereof at an optional ratio. These can be each obtained as a single product by synthesis methods and separation methods known per se. For example, an optical isomer can be obtained by using an optically active synthesis intermediate or by optical resolution of a synthesis intermediate or a racemate of the final product by a conventional method.

Sulfated polymer further encompasses stable isotopes and radioactive isotopes.

Examples of the sulfated polymer include, but are not limited to, sulfo group-containing polyvinyl alcohol (i.e., polyvinyl alcohol $SO_3H$), sulfo group-containing polyvinyl amine (i.e., polyvinyl amine $SO_3H$), polyethylene sulfonic acid, sulfo group-containing polyallylamine (i.e., polyallylamine $SO_3H$), sulfo group-containing polyethyleneimine (i.e., polyethyleneimine $SO_3H$), sulfo group-containing α-polylysine (i.e., α-polylysine $SO_3H$), sulfo group-containing α-poly methyl glutamate/α-5-hydroxynorvaline (2/8) copolymer (i.e., α-poly methyl glutamate/α-5-hydroxynorvaline (5-$SO_3H$) (2/8) copolymer), α-polyglutamic acid-γ-taurine, sulfo group-containing triserine (i.e., triserine $SO_3H$), sulfo group-containing serine (i.e., serine $SO_3H$), sulfo group-containing branched-polyglycerol (i.e., branched-polyglycerol $SO_3H$) and a derivative thereof and the like. Here, the derivative of sulfo group-containing branched-polyglycerol is a compound wherein any functional group is bonded to any substitutable position of sulfo group-containing branched-polyglycerol (i.e., branched-polyglycerol $SO_3H$). Specific examples of the derivative of sulfo group-containing branched-polyglycerol or a pharmaceutically acceptable salt thereof include branched-polyglycerol-monomethyltetraethyleneglycol-$SO_3Na$, branched-polyglycerol-2-furfuryl-$SO_3Na$, branched-polyglycerol-isopropyloxy-$SO_3Na$ and the like. The branched-polyglycerol-isopropyloxy-$SO_3Na$ is a novel compound. Preferred are sulfo group-containing polyvinyl alcohol, sulfo group-containing polyvinyl amine, polyethylene sulfonic acid, sulfo group-containing polyallylamine, sulfo group-containing α-poly methyl glutamate/α-5-hydroxynorvaline (2/8) copolymer, α-polyglutamic acid-γ-taurine and sulfo group-containing triserine.

The sulfated polymer to be contained in the medium of the present invention may be in the form of a pharmaceutically acceptable salt. Examples of such salt include a salt of a sulfo group and a base. Specific examples thereof include alkali metal salts such as sodium salt, potassium salt and the like; alkaline earth metal salts such as calcium salt, magnesium salt and the like; salts with inorganic base such as aluminum salt, ammonium salt and the like; salts with organic base such as trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like, which can be prepared from a free form by a conventional method. As the pharmaceutically acceptable salt of the sulfated polymer, a sodium salt of sulfo group is preferable. Examples thereof include polyvinyl alcohol $SO_3Na$, polyvinyl amine $SO_3Na$, polyethylene sulfonate Na and the like.

The weight-average molecular weight of the sulfated polymer or a pharmaceutically acceptable salt thereof is not particularly limited, and varies depending on the kind of the sulfated polymer to be employed and the kind of the salt. It is generally 200 to 400,000, preferably 500 to 100,000, more preferably 500 to 50,000. When the weight-average molecular weight exceeds 400,000, the solubility in a medium tends to decrease. The weight-average molecular weight can be measured by gel permeation chromatography and the like.

In one embodiment of the present invention, the sulfated compound is a sulfated substance of a saccharide polymer crosslinked by a diisocyanate compound or a pharmaceutically acceptable salt thereof. While saccharides are similar to those in the above-mentioned sulfated saccharides and are not particularly limited, preferred are maltotriose and dextran. While the diisocyanate compound is not particularly limited, for example, known aliphatic diisocyanate, alicyclic diisocyanate, alicyclic aromatic diisocyanate and aromatic diisocyanate can be mentioned. Preferred is aliphatic diisocyanate, and more preferred is hexamethylene diisocyanate. The sulfated substance of a saccharide polymer crosslinked by a diisocyanate compound or a pharmaceutically acceptable salt thereof is preferably maltotriose-hexamethylene diisocyanate-$SO_3Na$ or dextran-hexamethylene diisocyanate-$SO_3Na$.

The sulfated substance of a saccharide polymer crosslinked by a diisocyanate compound or a pharmaceutically acceptable salt thereof can be produced by a method known in the field. For example, maltotriose-hexamethylene diisocyanate-$SO_3Na$ and dextran-hexamethylene diisocyanate-$SO_3Na$ can be synthesized by the methods described in the below-mentioned Examples.

Maltotriose-hexamethylene diisocyanate-$SO_3Na$ is a novel compound.

In one embodiment of the present invention, the sulfated compound is a sulfated substance of sugar-lactone or a pharmaceutically acceptable salt thereof. The sugar-lactone refers to a cyclic ester compound induced by an oxidation reaction of saccharides. While saccharides are similar to those in the above-mentioned sulfated saccharides and are not particularly limited, examples thereof include monosaccharide, disaccharide and polysaccharide, with preference given to glucose. The sulfated substance of sugar-lactone or a pharmaceutically acceptable salt thereof is preferably gluconolactone-$SO_3Na$.

The sulfated substance of sugar-lactone or a pharmaceutically acceptable salt thereof can be produced by a method known in the field. For example, gluconolactone-$SO_3Na$ can be synthesized by the methods described in the below-mentioned Examples.

Gluconolactone-$SO_3Na$ is a novel compound.

In one embodiment of the present invention, the sulfated compound is a sulfated substance of an organic acid or a pharmaceutically acceptable salt thereof. The organic acid is not particularly limited as long as it has one or more substituents capable of sulfation such as hydroxyl group and the like. Examples thereof include malic acid, tartaric acid, citric acid and the like, with preference given to tartaric acid. The sulfated substance of an organic acid or a pharmaceutically acceptable salt thereof is preferably tartrate-$SO_3Na$.

The sulfated substance of an organic acid or a pharmaceutically acceptable salt thereof can be produced by a method known in the field. For example, tartrate-$SO_3Na$ can be synthesized by the methods described in the below-mentioned Examples.

The concentration of a sulfated compound or a pharmaceutically acceptable salt thereof in the medium of the present invention can be determined to fall within any range as long as it promotes the growth of a stem cell in the presence of FGF, and varies depending on the kind of the sulfated compound to be employed. When the concentration of a sulfated compound or a pharmaceutically acceptable salt thereof is low, the stem cell growth promoting effect in the presence of FGF is sometimes weakened and, when the concentration is high, cell proliferation is sometimes suppressed due to the cytotoxicity of the sulfated compound itself or adhesion inhibition. Therefore, the medium of the present invention characteristically contains a sulfated compound or a pharmaceutically acceptable salt thereof at a concentration promoting the growth of a stem cell in the presence of FGF.

For example, when the sulfated saccharide or a pharmaceutically acceptable salt thereof is a sulfated polysaccharide, the growth of stem cell can be promoted when the concentration thereof in the medium of the present invention is 2.5 pg/ml to 10 µg/ml, preferably 25 pg/ml to 250 ng/ml, in the presence of FGF.

For example, when the sulfated saccharide or a pharmaceutically acceptable salt thereof is a dextran sulfate Na (average molecular weight 2,500 to 7,000), the growth of stem cell can be promoted when the concentration thereof in the medium of the present invention is 2.5 pg/ml to 10 µg/ml, preferably 25 pg/ml to 2.5 µg/ml, in the presence of FGF.

For example, when the sulfated saccharide or a pharmaceutically acceptable salt thereof is a sucrose $8SO_3K$ (molecular weight 1,287), the growth of stem cell can be promoted when the concentration thereof in the medium of the present invention is 2.5 pg/ml to 25 µg/ml, preferably 25 pg/ml to 10 µg/ml, in the presence of FGF.

For example, when the sulfated saccharide or a pharmaceutically acceptable salt thereof is a mannitol $SO_3Na$ (maximum molecular weight 794), the growth of stem cell can be promoted when the concentration thereof in the medium of the present invention is 50 ng/ml to 200 ng/ml or 500 ng/ml to 100 µg/ml, preferably 75 ng/ml to 150 ng/ml or 2.5 µg/ml to 25 µg/ml, in the presence of FGF.

For example, when the sulfated saccharide or a pharmaceutically acceptable salt thereof is an alginate $SO_3Na$ (molecular weight 10,000 to 600,000), the growth of stem cell can be promoted when the concentration thereof in the medium of the present invention is 100 ng/ml to 10 µg/ml, preferably 250 ng/ml to 2.5 µg/ml, in the presence of FGF.

For example, when the sulfated saccharide or a pharmaceutically acceptable salt thereof is a fucoidan (molecular weight 200,000 to 1,000,000), the growth of stem cell can be promoted when the concentration thereof in the medium of the present invention is 2.5 ng/ml to 1.0 µg/ml, preferably 25 ng/ml to 250 ng/ml, in the presence of FGF.

For example, when the sulfated saccharide or a pharmaceutically acceptable salt thereof is a cellulose $SO_3Na$, the growth of stem cell can be promoted when the concentration thereof in the medium of the present invention is 250 pg/ml to 2.5 µg/ml, preferably 2.5 ng/ml to 250 ng/ml, in the presence of FGF.

For example, when the sulfated saccharide or a pharmaceutically acceptable salt thereof is a xanthan gum $SO_3Na$ (molecular weight not less than 2,000,000), the growth of stem cell can be promoted when the concentration thereof in the medium of the present invention is 2.5 pg/ml to 250 pg/ml or 5 ng/ml to 250 ng/ml, preferably 5 pg/ml to 200 pg/ml or 10 ng/ml to 250 ng/ml, in the presence of FGF.

For example, when the sulfated saccharide or a pharmaceutically acceptable salt thereof is a pectin $SO_3Na$, the growth of stem cell can be promoted when the concentration thereof in the medium of the present invention is 2.5 ng/ml to 500 ng/ml, preferably 25 ng/ml to 250 ng/ml, in the presence of FGF.

For example, when the sulfated saccharide or a pharmaceutically acceptable salt thereof is a maltoheptaose $SO_3Na$ (maximum molecular weight 3498), the growth of stem cell can be promoted when the concentration thereof in the medium of the present invention is 25 pg/ml to 250 ng/ml, preferably 250 pg/ml to 250 ng/ml, in the presence of FGF.

For example, when the sulfated saccharide or a pharmaceutically acceptable salt thereof is a xylitol $SO_3Na$ (maximum molecular weight 662), the growth of stem cell can be promoted when the concentration thereof in the medium of the present invention is 25 pg/ml to 2.5 µg/ml, preferably 250 pg/ml to 250 ng/ml, in the presence of FGF.

For example, when the sulfated saccharide or a pharmaceutically acceptable salt thereof is a meso-erythritol $SO_3Na$ (maximum molecular weight 530), the growth of stem cell can be promoted when the concentration thereof in the medium of the present invention is 25 pg/ml to 2.0 ng/ml or 5 ng/ml to ng/ml, preferably 25 pg/ml to 150 pg/ml or 25 ng/ml to 250 ng/ml, in the presence of FGF.

For example, when the sulfated saccharide or a pharmaceutically acceptable salt thereof is a maltotriose $SO_3Na$, the growth of stem cell can be promoted when the concentration thereof in the medium of the present invention is 2.5 pg/ml to 10 μg/ml, preferably 25 pg/ml to 2.5 μg/ml, in the presence of FGF.

For example, when the sulfated saccharide or a pharmaceutically acceptable salt thereof is a maltitol $SO_3Na$, the growth of stem cell can be promoted when the concentration thereof in the medium of the present invention is 10 ng/ml to 50 μg/ml, preferably 25 ng/ml to 2.5 μg/ml, in the presence of FGF.

For example, when the sulfated polymer or a pharmaceutically acceptable salt thereof is a polyvinyl alcohol $SO_3Na$, the growth of stem cell can be promoted when the concentration thereof in the medium of the present invention is 250 pg/ml to 200 ng/ml, preferably 250 pg/ml to 100 ng/ml, in the presence of FGF.

For example, when the sulfated polymer or a pharmaceutically acceptable salt thereof is a polyvinyl amine $SO_3Na$, the growth of stem cell can be promoted when the concentration thereof in the medium of the present invention is 5 ng/ml to 250 ng/ml, preferably 25 ng/ml to 250 ng/ml, in the presence of FGF.

For example, when the sulfated polymer or a pharmaceutically acceptable salt thereof is a polyethylene sulfonate Na, the growth of stem cell can be promoted when the concentration thereof in the medium of the present invention is 250 pg/ml to 250 ng/ml, preferably 25 ng/ml to 250 ng/ml, in the presence of FGF.

For example, when the sulfated polymer or a pharmaceutically acceptable salt thereof is a polyallylamine $SO_3Na$, the growth of stem cell can be promoted when the concentration thereof in the medium of the present invention is 12.5 pg/ml to 2 ng/ml or 5 ng/ml to 200 ng/ml, preferably 25 pg/ml to 250 pg/ml or 25 ng/ml to 100 ng/ml, in the presence of FGF.

For example, when the sulfated polymer or a pharmaceutically acceptable salt thereof is an α-poly methyl glutamate/α-5-hydroxynorvaline (5-$SO_3Na$) (2/8) copolymer, the growth of stem cell can be promoted when the concentration thereof in the medium of the present invention is 12.5 pg/ml to 2 ng/ml or 5 ng/ml to 250 μg/ml, preferably 25 pg/ml to 250 pg/ml or 25 ng/ml to 2.5 μg/ml, in the presence of FGF.

For example, when the sulfated polymer or a pharmaceutically acceptable salt thereof is an α-glutamic acid-γ-taurine Na, the growth of stem cell can be promoted when the concentration thereof in the medium of the present invention is 12.5 pg/ml to 2 ng/ml or 5 ng/ml to 250 μg/ml, preferably 25 pg/ml to 250 pg/ml or 25 ng/ml to 2.5 μg/ml, in the presence of FGF.

For example, when the sulfated polymer or a pharmaceutically acceptable salt thereof is a triserine $SO_3Na$, the growth of stem cell can be promoted when the concentration thereof in the medium of the present invention is 125 pg/ml to 5 ng/ml, preferably 250 pg/ml to 2.5 ng/ml, in the presence of FGF.

For example, when the sulfated polymer or a pharmaceutically acceptable salt thereof is a branched-polyglycerol $SO_3Na$, the growth of stem cell can be promoted when the concentration thereof in the medium of the present invention is 10 pg/ml to 1 μg/ml, preferably 25 pg/ml to 250 ng/ml, in the presence of FGF.

For example, when the sulfated polymer or a pharmaceutically acceptable salt thereof is a branched-polyglycerol-monomethyltetraethyleneglycol-$SO_3Na$, the growth of stem cell can be promoted when the concentration thereof in the medium of the present invention is 12.5 pg/ml to 12.5 ng/ml, preferably 25 pg/ml to 2.5 ng/ml, in the presence of FGF.

For example, when the sulfated polymer or a pharmaceutically acceptable salt thereof is a branched-polyglycerol-isopropyloxy-$SO_3Na$, the growth of stem cell can be promoted when the concentration thereof in the medium of the present invention is 12.5 pg/ml to 50 ng/ml, preferably 25 pg/ml to 25 ng/ml, in the presence of FGF.

For example, when the sulfated compound or a pharmaceutically acceptable salt thereof is a dextran-hexamethylene diisocyanate-$SO_3Na$, the growth of stem cell can be promoted when the concentration thereof in the medium of the present invention is 25 pg/ml to 2.0 ng/ml or 5 ng/ml to 100 ng/ml, preferably 25 pg/ml to 250 pg/ml or 10 ng/ml to 100 ng/ml, in the presence of FGF.

For example, when the sulfated compound or a pharmaceutically acceptable salt thereof is a maltotriose-hexamethylene diisocyanate-$SO_3Na$, the growth of stem cell can be promoted when the concentration thereof in the medium of the present invention is 25 pg/ml to 2.0 ng/ml or 100 ng/ml to 500 ng/ml, preferably 25 pg/ml to 250 pg/ml or 100 ng/ml to 250 ng/ml, in the presence of FGF.

For example, when the sulfated compound or a pharmaceutically acceptable salt thereof is a gluconolactone-$SO_3Na$, the growth of stem cell can be promoted when the concentration thereof in the medium of the present invention is 25 pg/ml to 2.0 ng/ml, preferably 25 pg/ml to 250 pg/ml, in the presence of FGF.

For example, when the sulfated compound or a pharmaceutically acceptable salt thereof is a tartrate-$SO_3Na$, the growth of stem cell can be promoted when the concentration thereof in the medium of the present invention is 500 pg/ml to 20 ng/ml, preferably 1 ng/ml to 10 ng/ml, in the presence of FGF.

The sulfated compound or a pharmaceutically acceptable salt thereof can suppress a decrease in the protein amount of FGF in a medium for stem cell proliferation. Here, the suppression of a decrease in the protein amount of FGF means that a decrease in the FGF protein amount is suppressed when, after incubation for a given time in the presence of a sulfated compound or a pharmaceutically acceptable salt thereof, the amount of FGF protein in the solution is measured immunoepidemiologically. Whether a decrease in the protein amount of FGF is suppressed can be evaluated by a known method such as the method described in the Examples and the like. For example, when the FGF protein amount after incubation under the conditions that renders the FGF protein amount after incubation less than 10% (for example, 37° C. for 7 days etc.) is not less than 10% (preferably not less than 30%, more preferably not less than 50%, most preferably not less than 70%), wherein the FGF protein amount after incubation under the conditions known to not decrease the FGF protein amount (for example, 4° C. for 7 days etc.) is 100%, a decrease in the FGF protein amount can be judged to have been suppressed.

Since a sulfated compound or a pharmaceutically acceptable salt thereof capable of suppressing a decrease in the protein amount of FGF tends to promote the growth of a stem cell in the presence of FGF, in order to select a sulfated compound or a pharmaceutically acceptable salt thereof to be subjected to a culture test, whether a sulfated compound or a pharmaceutically acceptable salt thereof suppresses a decrease in the protein amount of FGF may be evaluated before evaluation of whether a sulfated compound or a pharmaceutically acceptable salt thereof promotes the growth of stem cell in the presence of FGF. In some cases, however, the growth of a stem cell is not promoted in the presence of FGF even within a concentration range that suppresses a decrease in the protein amount of FGF, since suppression of cell proliferation appears strongly due to the cytotoxicity or adhesion inhibition of the sulfated compound or a pharmaceutically acceptable salt thereof. In some cases, moreover, the growth of a stem cell is promoted in the presence of FGF even within a concentration range where suppression of a decrease in the protein amount of FGF is not confirmed in the methods of Examples I-1 and II-1, which is caused by a weak suppression of a decrease in the protein amount of FGF or the action of other sulfated compounds. Therefore, the concentration range of a sulfated compound or a pharmaceutically acceptable salt thereof in the medium of the present invention is determined by a method using a cell proliferation system such as the method described in the Examples and the like.

In addition, depending on the kind of the sulfated compound, the concentration range of a sulfated compound or a pharmaceutically acceptable salt thereof in the medium of the present invention may be set to a low concentration that does not generally suppress a decrease in the protein amount of FGF, so as to reduce an influence on the cell such as cytotoxicity and the like.

For example, as shown in the below-mentioned Examples, a sulfated substance of sucrose or xylitol, or a salt thereof (e.g., sucrose $8SO_3K$, xylitol $SO_3Na$ and the like), when its concentration is not more than 2.5 µg/ml, does not suppress a decrease in the protein amount of FGF; however, it can promote the growth of stem cell in the presence of FGF even if its concentration range is 25 pg/ml to 2.5 µg/ml.

In addition, for example, a sulfated substance of polyvinyl amine or a salt thereof (e.g., polyvinyl amine $SO_3Na$), when its concentration is not more than 25 ng/ml, does not suppress a decrease in the protein amount of FGF; however, it can promote the growth of stem cell in the presence of FGF even if its concentration range is 10 ng/ml to 25 ng/ml (preferably 12.5 ng/ml to 25 ng/ml).

In addition, for example, a sulfated substance of polyallylamine or a salt thereof (e.g., polyallylamine $SO_3Na$), when its concentration is not more than 25 ng/ml, does not suppress a decrease in the protein amount of FGF; however, it can promote the growth of stem cell in the presence of FGF even if its concentration range is 12.5 pg/ml to 2 ng/ml or 5 ng/ml to 25 ng/ml (preferably 25 pg/ml to 250 pg/ml or 5 ng/ml to 25 ng/ml).

In addition, for example, a sulfated substance of α-poly methyl glutamate/α-5-hydroxynorvaline (2/8) copolymer or a salt thereof (e.g., α-poly methyl glutamate/5-hydroxy-α-norvaline (5-$SO_3Na$) (2/8) copolymer), when its concentration is not more than 25 µg/ml, does not suppress a decrease in the protein amount of FGF; however, it can promote the growth of stem cell in the presence of FGF even if its concentration range is 12.5 pg/ml to 2 ng/ml or 5 ng/ml to 20 µg/ml (preferably 25 pg/ml to 250 pg/ml or 25 ng/ml to 2.5 µg/ml).

In addition, for example, α-polyglutamic acid-γ-taurine or a salt thereof (e.g., α-polyglutamic acid-γ-taurine Na), when its concentration is not more than 2.5 µg/ml, does not suppress a decrease in the protein amount of FGF; however, it can promote the growth of stem cell in the presence of FGF even if its concentration range is 12.5 pg/ml to 2 ng/ml or 5 ng/ml to 20 µg/ml (preferably 25 pg/ml to 250 pg/ml or 25 ng/ml to 2.5 µg/ml).

In addition, for example, a sulfated substance of triserine or a salt thereof (e.g., triserine $SO_3Na$), when its concentration is not more than 2.5 µg/ml, does not suppress a decrease in the protein amount of FGF; however, it can promote the growth of stem cell in the presence of FGF even if its concentration range is 125 pg/ml to 5 ng/ml (preferably 250 pg/ml to 2.5 ng/ml).

In addition, for example, dextran-hexamethylene diisocyanate-$SO_3Na$, when its concentration is not more than 25 ng/ml, does not suppress a decrease in the protein amount of FGF; however, it can promote the growth of stem cell in the presence of FGF even if its concentration range is 25 pg/ml to 2.0 ng/ml or 5 ng/ml to 25 ng/ml.

In addition, for example, maltotriose-hexamethylene diisocyanate-$SO_3Na$, when its concentration is not more than 250 pg/ml, does not suppress a decrease in the protein amount of FGF; however, it can promote the growth of stem cell in the presence of FGF even if its concentration range is 25 pg/ml to 250 pg/ml.

In addition, for example, gluconolactone-$SO_3Na$, when its concentration is not more than 2.5 µg/ml, does not suppress a decrease in the protein amount of FGF; however, it can promote the growth of stem cell in the presence of FGF even if its concentration range is 25 pg/ml to 2.0 ng/ml.

In addition, for example, tartarte-$SO_3Na$, when its concentration is not more than 250 µg/ml, does not suppress a decrease in the protein amount of FGF; however, it can promote the growth of stem cell in the presence of FGF even if its concentration range is 500 pg/ml to 20 ng/ml.

For example, as shown in the below-mentioned Examples, a sulfated polymer requires an addition concentration at an order of ng to µg/ml to suppress a decrease in the protein amount of FGF. However, it can promote the growth of stem cell in the presence of FGF even at an addition concentration of pg/ml.

The medium of the present invention contains a fibroblast growth factor (FGF). Examples of the FGF include basic fibroblast growth factor (bFGF), acidic fibroblast growth factor (aFGF) and the like. Use of bFGF is preferable in the medium of the present invention since it shows a high promoting effect on the growth of stem cell.

FGF may be derived from any animal (e.g., rat, mouse, guinea pig, rabbit, sheep, horse, swine, bovine, monkey, human and the like), which can be selected as appropriate depending on the kind of the stem cell to be cultured. When a stem cell derived from human is cultivated, an FGF derived from human is preferable. Examples of the FGF include human bFGF (see, for example, Endocrine Rev., 8, 95, 1987, which is incorporated herein by reference in its entirety), bovine bFGF (see, for example, Proc. Natl. Acad. Sci. USA, 81, 6963, 1984, which is incorporated herein by reference in its entirety), mouse b FGF (see, for example, Dev. Biol., 138, 454-463, 1990, which is incorporated herein by reference in its entirety), rat b FGF (see, for example, Biochem. Biophys. Res. Commun., 157, 256-263, 1988, which is incorporated herein by reference in its entirety) and the like.

FGF to be contained in the medium of the present invention includes isolated/purified natural, synthetic or recombined protein, variant protein (including inserted, substituted and defective variants), fragment and chemically modified derivatives thereof, as long as it can promote the growth of a stem cell.

The concentration of FGF to be contained in the medium of the present invention is not particularly limited as long as it can promote the growth of a stem cell. When added to a medium, the concentration of FGF is generally 1 ng/ml to 300 ng/ml, preferably 1 ng/ml to 200 ng/ml, more preferably 4 ng/ml to 100 ng/ml. When the concentration of FGF is less than 1 ng/ml, the stem cell growth promoting effect tends to be unattained even in the presence of a sulfated compound. When the concentration of FGF exceeds 300 ng/ml, the culture cost tends to be high.

In the present invention, the term "stem cell" means an immature cell having self-renewal capacity and differentiation/proliferation capacity. The stem cell includes subpopulation such as pluripotent stem cell, multipotent stem cell, unipotent stem cell and the like, according to the differentiation potency. The pluripotent stem cell means a cell capable of differentiating into any tissue or cell constituting living organisms. The multipotent stem cell means a cell capable of differentiating into plural, though not all, kinds of tissues and cells. The unipotent stem cell means a cell capable of differentiating into particular tissues and cells.

Examples of the pluripotent stem cell include embryonic stem cells (ES cell), embryonic germ cell (EG cell), induced pluripotent stem cell (iPS cell) and the like. A stem cell established by cultivating an early embryo generated by nuclear transplantation of the nucleus of a somatic cell is also preferable as the pluripotent stem cell (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999); Nature Genetics, 24, 109 (2000) all of which are incorporated herein by reference in their entireties).

Examples of the multipotent stem cell include somatic stem cells such as mesenchymal stem cells, hematopoietic stem cells, neural stem cells, myeloid stem cells, germ line stem cells and the like, and the like. The multipotent stem cell is preferably a mesenchymal stem cell, more preferably a bone marrow mesenchymal stem cell. The mesenchymal stem cell broadly means a population of stem cells or progenitor cells thereof, which can differentiate into all or some of the mesenchymal cells such as osteoblast, chondroblast, lipoblast and the like.

While the medium of the present invention can be preferably used for proliferation of any stem cells, it is preferably used for proliferation of mesenchymal stem cells (e.g., bone marrow mesenchymal stem cells etc.), embryonic stem cells or induced pluripotent stem cells.

Also, the medium of the present invention can be preferably used for proliferation of stem cells derived from any animal. The stem cells cultured by using the medium of the present invention are, for example, pluripotent stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, *Macaca mulatta*, marmoset, orangutan, chimpanzee and the like. Preferred are stem cells derived from primates and the like.

As the basal medium of the present invention, one known per se can be used depending on the kind of the stem cells, and is not particularly limited as long as it does not inhibit proliferation of the stem cells. Examples thereof include DMEM, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, E8 medium (Nature Methods, 2011, 8, 424-429), ReproFF2 medium (ReproCELL Inc), a mixed medium thereof and the like. In addition, a medium altered for culture of stem cells, a mixture of the above-mentioned basal medium and other medium (e.g., DMEM including mesenchymal stem cell medium (MSCGM) described in the Examples etc.), and the like may also be used.

The medium of the present invention can contain an additive known per se. The additive is not particularly limited as long as it does not inhibit proliferation of stem cells. Examples thereof include growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like. In addition, additives that have been conventionally used for culturing stem cells can be contained as appropriate. The additive is preferably contained within a concentration range known per se.

The medium of the present invention may contain a serum. The serum is not particularly limited as long as it is derived from an animal and does not inhibit the growth of stem cells. Preferred is a mammal-derived serum (for example, fetal bovine serum, human serum etc.). The concentration of the serum may be any as long as it is within a concentration range known per se. However, a lower content of serum is more preferable, and the absence of serum is most preferable, since it is known that serum components also contain a differentiation factor of human ES cell, and the like, and the culture results may be inconsistent due to a difference between serum lots. Furthermore, when a stem cell after culture is used for medical purposes, a xeno-derived component may become an infection source of blood-mediated pathogen or a heterogeneous antigen. Therefore, the absence of serum is preferable. When serum is not contained, a replacement additive of serum (for example, Knockout Serum Replacement (KSR) (Invitrogen), Chemically-defined Lipid concentrated (Gibco) etc.) may also be used.

The present invention further provides a culture method of stem cell using a medium containing FGF for stem cell proliferation, which comprises adding a sulfated compound or a pharmaceutically acceptable salt thereof to a medium (hereinafter to be also referred to as the method of the present invention).

The sulfated compound or a pharmaceutically acceptable salt thereof, FGF, stem cell and medium are as mentioned above.

The method of the present invention characteristically comprises adding a sulfated compound or a pharmaceutically acceptable salt thereof to the medium at a concentration promoting the growth of a stem cell in the presence of FGF. The addition concentration of a sulfated compound or a pharmaceutically acceptable salt thereof to a medium is not particularly limited as long as it can promote the growth of a stem cell in the presence of FGF.

A sulfated compound or a pharmaceutically acceptable salt thereof may be added to a medium before or after contact of the medium and a stem cell. Also, it may be added as appropriate to a medium during culture of a stem cell.

In the method of the present invention, the medium may be exchanged as appropriate during culture. In this case, a sulfated compound or a pharmaceutically acceptable salt thereof is also added to the new medium at a concentration promoting the growth of a stem cell in the presence of FGF.

The concentration of FGF in the medium is not particularly limited as long as it can promote the growth of a stem cell. It is generally 1 ng/ml to 300 ng/ml, preferably 1 ng/ml to 200 ng/ml, more preferably 4 ng/ml to 100 ng/ml, at the time of addition of FGF to the medium. When the FGF concentration is less than 1 ng/ml, the stem cell growth promoting effect tends to be unattainable even in the presence of a sulfated compound. When the FGF concentration exceeds 300 ng/ml, the culture cost tends to be high.

FGF may be added to a medium before or after contact of the medium and a stem cell, or before or after adding a sulfated compound or a pharmaceutically acceptable salt thereof to a medium. Also, it may be added as appropriate to a medium during culture of a stem cell.

The medium of the present invention is added with a sulfated compound in advance, and can be preferably used for the culture method of the present invention since the culture steps can be reduced.

While a culture container to be used for the culture of stem cell is not particularly limited as long as stem cells can be cultured, a flask, tissue culture flask, dish, petri dish, tissue culture dish, multidish, microplate, microwell plate, multiplate, multiwell plate, microslide, chamber slide, petri dish, tube, tray, culture bag and roller bottle can be mentioned.

The culture container may be cell adhesive or cell non-adhesive, and is appropriately selected according to the object. A cell adhesive culture container may be coated with any cell supporting substrate such as extracellular matrix (ECM, also referred to as an extracellular substrate) and the like, in an attempt to improve the adhesiveness of the culture container surface to a cell. The cell supporting substrate may be any substance aiming at adhesion of stem cell or feeder cell (when used).

When a feeder cell is not used, culture is preferably performed by using an extracellular matrix or an active fragment thereof or an artificial product mimicking the functions thereof.

The extracellular matrix is not particularly limited as long as it is generally used for cell culture with the aim to improve adhesion between the surface of a culture container and the cell. For example, known ones such as laminin (laminin 511, laminin 332 etc.), fibronectin, vitronectin, collagen, elastin, adhesamine and the like can be used. The active fragment of an extracellular matrix only needs to be a fragment thereof having a cell adhesion activity equivalent to that of the extracellular matrix, and known ones can be used. For example, E8 fragment of laminin 511, E8 fragment of laminin 332 and the like disclosed in JP-A-2011-78370, which is incorporated herein by reference in its entirety, can be mentioned. The extracellular matrix and an active fragment thereof may be commercially available products and available from, for example, (Life Technologies, BD Falcon, BioLamina) and the like. Two or more kinds of these extracellular matrices and active fragments thereof may be used in combination. Also, a matrigel (trade name) which is a mixture of complicated basal lamina components containing protein and polysaccharides, that are extracted and purified from EHS sarcoma of mouse overproducing the basal lamina, may also be used. The extracellular matrix and an active fragment thereof may be suspended in a suitable solution, and applied to a container suitable for cultivating cells.

An artificial product mimicking the function of extracellular matrix is not particularly limited as long as it is generally used for culturing cells and, for example, known ones such as Synthemax (registered trade mark) and Ultra-Web (registered trade mark) of Corning Incorporated, Hy-STEM series, polylysine and polyornithine of Sigma Aldrich Co., Ltd. and the like can be used.

The extracellular matrix or an active fragment thereof or an artificial product mimicking the functions thereof to be used in the present invention are preferably matrigel or laminin 511 or an active fragment of laminin 511, more preferably an active fragment of laminin 511 (i.e., 58 fragment of laminin 511).

In the culture method of the present invention, the cell seeding method is not particularly limited. When a pluripotent stem cell is cultivated, it may be colony seeding or single cell-seeding. To produce pluripotent stem cells for regenerative medicine at an industrial level, the work needs to be performed by plural workers under the conditions where procedures and schedule are rigorously managed. Therefore, single cell-seeding permitting rigorous adjustment of the seeding cell number is preferable.

For single cell-seeding, colonies of pluripotent stem cells are dissociated to single cells, and seeded in the medium. Single cell seeding can be performed by a method known per se. For example, cell-cell adhesion and cell-matrix adhesion are weakened with a cell detaching solution (trypsin solution etc.), and the cells are detached from the matrix with a scraper (IWAKI, 9000-220 etc.) and the like (in this state, the cells forming cell clusters are suspended in a solution, not complete single cells). The cells are thereafter dissociated by pipetting into single cells, and seeded in the medium. When seeding, a ROCK inhibitor such as Y-27632 (Nacalai Tesque: 08945-84) and the like is preferably added to the medium to ensure survival of the pluripotent stem cells. From the day following the seeding, it is preferably excluded from the medium since a ROCK inhibitor is not necessary for the proliferation of pluripotent stem cells.

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen partial pressure can be 1 to 10%.

Other features of the invention will become apparent in the course of the following descriptions of exemplary embodiments which are given for illustration of the invention and are not intended to be limiting thereof.

EXAMPLES

I. Evaluation of Sulfated Saccharides, Sulfated Substance of Saccharide Polymer Crosslinked by Diisocyanate Compound, Sulfated Substance of Sugar-Lactone, and Sulfated Substance of Organic Acid

Synthetic Example 1. Synthesis of Cellulose $SO_3Na$ (Cellulose Sulfate Na)

Cellulose (200 mg, Manufactured by Merck) was dissolved in dehydrated dimethylformamide (6 ml), sulfur trioxide trimethylamine complex (600 mg, manufactured by Aldrich) was added, and the mixture was stirred at 70° C. overnight. The solvent was removed by decantation, acetone was added, and the mixture was stirred and filtered. The obtained solid was dissolved in pure water (2 ml), 30% aqueous sodium acetate solution (1.5 ml) was added, and the mixture was stirred at room temperature for 2 hours. Ethanol (12 ml) was added to the reaction mixture, and the precipitate was collected by filtration. The obtained solid was dissolved in pure water (5 ml), dialyzed overnight using Spectra/Por MWCO 6,000-8,000, and freeze-dried to give a white solid (425 mg).

Synthetic Examples 2-4. Synthesis of Xanthan Gum $SO_3Na$ (Xanthan Gum Sulfate Na), Alginate $SO_3Na$ and Inulin $SO_3Na$ The following compounds were also subjected to sodium sulfatization under the conditions similar to those for cellulose $SO_3Na$.

TABLE 1

Sulfation of polysaccharides.

| compound | starting material | Synthetic Example | yield (mg) |
|---|---|---|---|
| xanthan gum $SO_3Na$ | Tokyo Chemical Industry Co., Ltd. | 2 | 330 |
| alginate $SO_3Na$ | Tokyo Chemical Industry Co., Ltd. | 3 | 175 |
| inulin $SO_3Na$ | Tokyo Chemical Industry Co., Ltd. | 4 | 158 |

Synthetic Example 5. Synthesis of α-Cyclodextrin $SO_3Na$ (α-CD.$SO_3Na$)

α-Cyclodextrin (α-CD) (200 mg, manufactured by Junsei chemical) was dissolved in dehydrated dimethylformamide (6 ml), sulfur trioxide trimethylamine complex (600 mg) was added, and the mixture was stirred at 70° C. overnight. The solvent was removed by decantation, acetone was added, and the mixture was stirred and filtered. The obtained solid was dissolved in pure water (2 ml), 30% aqueous sodium acetate solution (1.5 ml) was added, and the mixture was stirred at room temperature for 2 hours. Ethanol (12 ml) was added to the reaction mixture, and the precipitate was collected by filtration. The obtained solid was dissolved in pure water (5 ml), dialyzed overnight using Spectra/Por MWCO 1,000, and freeze-dried to give a white solid (598 mg).

Synthetic Examples 6-8. Synthesis of Maltoheptaose $SO_3Na$, Stachyose $SO_3Na$, Maltotriose $SO_3Na$ The following compounds were also subjected to sodium sulfatization under the conditions similar to those for α-cyclodextrin $SO_3Na$. Spectra/Por MWCO 100-500 was used for dialysis in Synthetic Examples 6-8.

TABLE 2

Sulfation of saccharides.

| compound | starting material | Synthetic Example | yield (mg) |
|---|---|---|---|
| maltoheptaose $SO_3Na$ | Tokyo Chemical Industry Co., Ltd. | 6 | 412 |
| stachyose $SO_3Na$ | Tokyo Chemical Industry Co., Ltd. | 7 | 141 |
| maltotriose $SO_3Na$ | Tokyo Chemical Industry Co., Ltd. | 8 | 240 |

Synthetic Example 9. Synthesis of Maltitol $SO_3Na$

Maltitol (300 mg, manufactured by Tokyo Chemical Industry Co., Ltd.) was dissolved in dehydrated dimethylformamide (6 ml), sulfur trioxide trimethylamine complex (1.6 g) was added, and the mixture was stirred at 70° C. overnight. The reaction mixture was concentrated, ethanol was added, and the mixture was stirred and filtered. The obtained solid was dissolved in water, sodium hydrogen carbonate was added, and the mixture was adjusted to pH 7 and stirred. The mixture was concentrated three times and freeze-dried to give a white solid (1.17 g).

Synthetic Example 11. Synthesis of Mannitol $SO_3Na$

Mannitol (200 mg, manufactured by KANTO CHEMICAL CO., INC.) was dissolved in dehydrated dimethylformamide (6 ml), sulfur trioxide trimethylamine complex (600 mg) was added, and the mixture was stirred at 70° C. overnight. 2N Aqueous sodium hydroxide solution was added to the reaction mixture to adjust to pH 9 and the mixture was concentrated. The residue was carried on a gel filtration column (Bio-Gel p-2, manufactured by Bio-Rad, Richmond, Calif.), and eluted with 0.1M aqueous ammonium hydrogen carbonate solution. The eluate was freeze-dried to give a white solid (43 mg).

Synthetic Examples 10 and 12-14. Synthesis of Glucose $SO_3Na$, Xylitol $SO_3Na$, Erythritol $SO_3Na$, Glycerol $SO_3Na$ The following compounds were also subjected to sodium sulfatization under the conditions similar to those for mannitol $SO_3Na$.

TABLE 3

Sulfation of saccharides.

| compound | starting material | Synthetic Example | yield (mg) |
|---|---|---|---|
| glucose SO₃Na | Junsei Chemical Co., Ltd. | 10 | 900 |
| Xylitol SO₃Na | Tokyo Chemical Industry Co., Ltd. | 12 | 950 |
| erythritol SO₃Na | Tokyo Chemical Industry Co., Ltd. | 13 | 300 |
| glycerol SO₃Na | NACALAI TESQUE, INC. | 14 | 883 |

Synthetic Example 15. Synthesis of Maltotriose-Hexamethylene Diisocyanate-SO₃Na

Maltotriose (200 mg, manufactured by Tokyo Chemical Industry Co., Ltd.) and triethylamine (28 μl, manufactured by Junsei Chemical Co., Ltd.) were added to dehydrated dimethylformamide (6 ml), and the mixture was stirred at 70° C. Hexamethylene diisocyanate (96 μl, manufactured by Tokyo Chemical Industry Co., Ltd.) was added, and the mixture was stirred overnight. The reaction mixture was concentrated, water was added, and the mixture was concentrated and freeze-dried to give a white solid (102 mg).

The obtained white solid (102 mg) was also subjected to sodium sulfatization under the conditions similar to those in Synthetic Example 1 and using dehydrated dimethylformamide (3 ml) and sulfur trioxide trimethylamine complex (460 mg) to give a white solid (332 mg).

Synthetic Example 16. Synthesis of Dextran-Hexamethylene Diisocyanate-SO₃Na

Dextran (200 mg, manufactured by Wako Pure Chemical Industries, Ltd.) and triethylamine (8.4 μl, manufactured by Junsei Chemical Co., Ltd.) were added to dehydrated dimethylformamide (200 ml), and the mixture was stirred at 70° C. Hexamethylene diisocyanate (9.6 μl, manufactured by Tokyo Chemical Industry Co., Ltd.) was added, and the mixture was stirred overnight. The reaction mixture was concentrated, water was added, and the mixture was concentrated and freeze-dried to give a white solid (193 mg).

The obtained white solid (100 mg) was also subjected to sodium sulfatization under the conditions similar to those in Synthetic Example 1 and using dehydrated dimethylformamide (20 ml) and sulfur trioxide trimethylamine complex (1 g) to give a white solid (194 mg).

Synthetic Example 17. Synthesis of Gluconolactone-SO₃Na

δ-Gluconolactone (300 mg, manufactured by Junsei Chemical Co., Ltd.) was dissolved in dehydrated dimethylformamide (6 ml), sulfur trioxide trimethylamine complex (1.14 g) was added, and the mixture was stirred at 70° C. overnight. The solvent was evaporated, and the residue was slurry-washed with acetone and ethanol. An aqueous sodium hydrogen carbonate solution was added to the residue, and the mixture was stirred. The reaction mixture was concentrated, carried on ion exchange resin IRA96SBAG, eluted with 0.2N sodium hydroxide (100 ml), carried on FPC3500, eluted with water (100 ml), concentrated and dried to give a yellow-brown solid (140 mg).

Synthetic Example 18. Synthesis of Tartrate-SO₃Na

Tartaric acid (300 mg, manufactured by Wako Pure Chemical Industries, Ltd.) was dissolved in dehydrated dimethylformamide, sulfur trioxide trimethylamine complex (835 mg) was added, and the mixture was stirred at 70° C. overnight. The solvent was evaporated, and the residue was carried on ion exchange resin IRA96SB, and eluted with 1% aqueous triethylamine solution (200 ml). The eluate was carried on ion exchange resin FPC3500, eluted with water (100 ml), concentrated and dried to give a white solid (430 mg).

Example I-1. Evaluation of bFGF Stabilization in Medium

1. Evaluation of bFGF Stabilization in Lonza Serum-Free Medium
(1) Preparation of Sample for bFGF Stabilization Evaluation.

As regards the stabilization of bFGF in a medium prepared using a Lonza dedicated complete synthetic medium kit (00190632, TAKARA BIO INC.) and according to the protocol (Lonza serum-free medium), the influence of the addition of the test compounds described in Table 4 was evaluated. A test compound was dissolved in phosphate buffered saline, and diluted 10-fold with a serum-free medium to adjust to the concentrations shown in Table 4 (test sample). The test sample was left standing in a tightly sealed Falcon tube at 37° C. for 7 days (Tables 5 to 8-2) or 3 days (Table 8-3), and the bFGF concentration was quantified by ELISA measurement. A phosphate buffered saline without a test compound was diluted 10-fold with a serum-free medium, and left standing at 37° C. or 4° C. for 7 days or 3 days, and used as a control.

TABLE 4

Test compound and evaluation concentration.

| | | 250 pg/ml | 2.5 ng/ml | 25 ng/ml | 250 ng/ml | 2.5 μg/ml | 25 μg/ml | 250 μg/ml | 2.5 mg/ml |
|---|---|---|---|---|---|---|---|---|---|
| dextran SO3Na (5000) | Wako Pure Chemical Industries, Ltd. | ○ | ○ | ○ | ○ | ○ | ○ | | |
| dextran SO3Na (25000) | Tokyo Chemical Industry Co., Ltd. | ○ | ○ | ○ | ○ | ○ | ○ | | |
| dextran SO3Na (500,000) | Wako Pure Chemical Industries, Ltd. | ○ | ○ | ○ | ○ | ○ | ○ | | |
| dextran 15000 | Wako Pure Chemical Industries, Ltd. | ○ | ○ | ○ | ○ | ○ | ○ | | |
| dextrin | Junsei Chemical Co., Ltd. | ○ | ○ | ○ | ○ | ○ | ○ | | |
| carageenan | NACALAI TESQUE, INC. | | ○ | ○ | ○ | ○ | ○ | ○ | |
| cellulose SO3Na | Synthetic Example 1 | | ○ | ○ | ○ | ○ | ○ | | |
| xanthan gum SO3Na | Synthetic Example 2 | | | ○ | ○ | ○ | ○ | | |
| xanthan gum | Tokyo Chemical Industry Co., Ltd. | | | ○ | ○ | ○ | ○ | | |
| fucoidan | funakoshi | | ○ | ○ | ○ | ○ | ○ | | |
| alginate SO3Na | Synthetic Example 3 | | ○ | ○ | ○ | ○ | ○ | | |
| alginate Na | Tokyo Chemical Industry Co., Ltd. | | | | | | ○ | ○ | ○ |
| inulin SO3Na | Synthetic Example 4 | | | ○ | ○ | ○ | ○ | ○ | |

TABLE 4-continued

Test compound and evaluation concentration.

| | | 250 pg/ml | 2.5 ng/ml | 25 ng/ml | 250 ng/ml | 2.5 µg/ml | 25 µg/ml | 250 µg/ml | 2.5 mg/ml |
|---|---|---|---|---|---|---|---|---|---|
| inulin | Tokyo Chemical Industry Co., Ltd. | | | | | | ○ | ○ | ○ |
| maltoheptaose SO3Na | Synthetic Example 6 | | ○ | ○ | ○ | ○ | ○ | ○ | ○ |
| α-cyclodextrin SO3Na | Synthetic Example 5 | | | ○ | ○ | ○ | ○ | ○ | |
| α-cyclodextrin | Junsei Chemical Co., Ltd. | | | | ○ | ○ | ○ | | |
| stachyose SO3Na | Synthetic Example 7 | | | ○ | ○ | ○ | ○ | ○ | ○ |
| maltotriose SO3Na | Synthetic Example 8 | | | ○ | ○ | ○ | ○ | ○ | ○ |
| maltotriose | Tokyo Chemical Industry Co., Ltd. | | | ○ | ○ | ○ | ○ | ○ | ○ |
| maltitol SO3Na | Synthetic Example 9 | | | ○ | ○ | ○ | ○ | ○ | ○ |
| maltitol | Tokyo Chemical Industry Co., Ltd. | | | ○ | ○ | ○ | ○ | ○ | ○ |
| sucrose 8SO3K | carbosynth | | | ○ | ○ | ○ | ○ | ○ | ○ |
| sucrose | Junsei Chemical Co., Ltd. | | | ○ | ○ | ○ | ○ | ○ | ○ |
| glucose SO3Na | Synthetic Example 10 | | | ○ | ○ | ○ | ○ | ○ | ○ |
| mannitol SO3Na | Synthetic Example 11 | | | ○ | ○ | ○ | ○ | ○ | ○ |
| mannitol | KANTO CHEMICAL CO., INC. | | | ○ | ○ | ○ | ○ | ○ | ○ |
| xylitol SO3Na | Synthetic Example 12 | | | ○ | ○ | ○ | ○ | ○ | ○ |
| xylitol | Tokyo Chemical Industry Co., Ltd. | | | ○ | ○ | ○ | ○ | ○ | |
| erythritol SO3Na | Synthetic Example 13 | | | ○ | ○ | ○ | ○ | | |
| glycerol SO3Na | Synthetic Example 14 | | | ○ | ○ | ○ | ○ | ○ | ○ |
| myo-inositol 6SO3K | Sigma Ltd. | | | ○ | ○ | ○ | ○ | ○ | ○ |
| maltotriose-hexamethylene diisocyanate-SO3Na | Synthetic Example 15 | ○ | ○ | ○ | ○ | ○ | ○ | ○ | ○ |
| dextran-hexamethylene diisocyanate-SO3Na | Synthetic Example 16 | | | ○ | ○ | ○ | ○ | ○ | ○ |
| gluconolactone-SO3Na | Synthetic Example 17 | | | ○ | ○ | ○ | ○ | ○ | ○ |
| tartrate-SO3Na | Synthetic Example 18 | | | ○ | ○ | ○ | ○ | ○ | ○ |

(2) Quantification of bFGF in Medium (ELISA Measurement)

A commercially available measurement kit (human bFGF ELISA kit, ELH-bFGF-001, Ray Biotech) was used for quantification of bFGF in the medium. The measurement procedures followed the protocol attached to the kit. The bFGF concentration of the serum-free medium was calculated from the analytical curve (conversion formula) drawn from the absorbance of an analytical curve standard solution. The evaluation criteria of Tables 5-8 are as follows:

+++: bFGF concentration was not less than 70% relative to that of 4° C. control

++: bFGF concentration was not less than 50% and less than 70% relative to that of 4° C. control +: bFGF concentration was not less than 30% and less than 50% relative to that of 4° C. control −: bFGF concentration was not less than 10% and less than 30% relative to that of 4° C. control x: bFGF concentration was less than 10% relative to that of 4° C. control

TABLE 5

Results of ELISA.

| | pg | ng | | µg | | | |
|---|---|---|---|---|---|---|---|
| | 250 | 2.5 | 25 | 250 | 2.5 | 25 | |
| dextran sulfate (5000) | ++ | ++ | ++ | ++ | +++ | + | |
| dextran sulfate (25000) | | ++ | ++ | +++ | ++ | ++ | |
| dextran sulfate (500,000) | x | − | + | ++ | ++ | + | |
| dextran 15000 | x | x | x | x | x | x | Comp. Ex. |
| dextrin | x | x | x | x | x | x | Comp. Ex. |
| carageenan | | x | x | x | + | + | |
| cellulose sulfate Na | | + | + | ++ | + | + | |
| xanthan gum sulfate Na | | | + | + | + | − | |
| xanthan gum | | x | x | x | x | | Comp. Ex. |
| fucoidan | | ++ | ++ | ++ | ++ | ++ | |
| alginate SO3Na | | + | ++ | + | + | ++ | |
| alginiate Na | | | | | | x | Comp. Ex. |
| inulin SO3Na | | ++ | + | + | + | ++ | |
| inulin | | | | | | x | Comp. Ex. |

4° C. ctrl ratio
+++ not less than 70%,
++ not less than 50%,
+ not less than 30%,
− not less than 10%,
x less than 10%

TABLE 6

Results of ELISA.

| | ng | | µg | | mg | |
|---|---|---|---|---|---|---|
| | 25 | 250 | 2.5 | 25 | 250 | 2.5 |
| maltoheptaose SO3Na | + | x | +++ | +++ | ++ | +++ |
| α-CD•SO3Na | x | + | ++ | − | + | |
| α-CD | | | | x | x | Comp. Ex. |
| stachyose SO3Na | x | − | +++ | +++ | +++ | +++ |

TABLE 6-continued

Results of ELISA.

|  | ng | | µg | | mg | |  |
|---|---|---|---|---|---|---|---|
|  | 25 | 250 | 2.5 | 25 | 250 | 2.5 |  |
| maltotriose SO3Na | x | x | + | + | +++ | +++ |  |
| maltotriose | x | x | x | x | x | x | Comp. Ex. |
| maltitol SO3Na | x | ++ | +++ | +++ | ++ | +++ |  |
| maltitol | x | x | x | x | x | x | Comp. Ex. |
| sucrose SO3Na | x | x | x | − | + | + |  |
| sucrose | x | x | x | x |  |  | Comp. Ex. |
| glucose SO3Na | x | x | x | x | − | + |  |

4° C. ctrl ratio
+++ not less than 70%,
++ not less than 50%,
+ not less than 30%,
− not less than 10%,
x less than 10%

TABLE 7

Results of ELISA.

|  | ng | | µg | | mg | |  |
|---|---|---|---|---|---|---|---|
|  | 25 | 250 | 2.5 | 25 | 250 | 2.5 |  |
| mannitol SO3Na | + | − | + | + | ++ | − |  |
| mannitol | x | x | x | x | x | x | Comp. Ex. |
| xylitol SO3Na | x | x | x | x | ++ | +++ |  |
| xylitol | x | x | x | x | x | x | Comp. Ex. |
| erythritol SO3Na | x | x | x | x | + | + |  |
| glycerol SO3Na | x | x | x | x | x | + |  |

4° C. ctrl ratio
+++ not less than 70%,
++ not less than 50%,
+ not less than 30%,
− not less than 10%,
x less than 10%

TABLE 8-1

Results of ELISA.

|  | ng | | µg | | mg | |
|---|---|---|---|---|---|---|
|  | 25 | 250 | 2.5 | 25 | 250 | 2.5 |
| myo-inositol 6SO3K | x | x | x | + | ++ | +++ |

4° C. ctrl ratio
+++ not less than 70%,
++ not less than 50%,
+ not less than 30%,
− not less than 10%,
x less than 10%

TABLE 8-2

Results of ELISA.

|  | pg | ng | | µg | | mg | |
|---|---|---|---|---|---|---|---|
|  | 250 | 2.5 | 25 | 250 | 2.5 | 25 | 250 | 2.5 |
| maltotriose-hexamethylene diisocyanate-SO3Na | − | ++ | x | + | + | + | ++ | + |

TABLE 8-2-continued

Results of ELISA.

|  | pg | ng | | µg | | mg | |
|---|---|---|---|---|---|---|---|
|  | 250 | 2.5 | 25 | 250 | 2.5 | 25 | 250 | 2.5 |
| dextran-hexamethylene diisocyanate-SO3Na |  | − | +++ | ++ | + | ++ | + |
| gluconolactone-SO3Na |  | x | x | x | ++ | x | +++ |
| tartrate-SO3Na |  | x | − | x | x | x | ++ |

4° C. ctrl ratio
+++ not less than 70%,
++ not less than 50%,
+ not less than 30%,
− not less than 10%,
x less than 10%

TABLE 8-3

Results of ELISA (37° C. for 3 days).

|  | ng | | µg | | mg | |
|---|---|---|---|---|---|---|
|  | 25 | 250 | 2.5 | 25 | 250 | 2.5 |
| meso-erythritol SO3Na | x | x | x | ++ | +++ | ++ |
| sucrose 8SO3K | x | − | +++ | +++ | +++ | ++ |
| Maltoheptaose SO3Na | − | ++ | ++ | ++ | ++ | +++ |

4° C. ctrl ratio
+++ not less than 70%,
++ not less than 50%,
+ not less than 30%,
− not less than 10%,
x less than 10%

As shown in Tables 5-8, incubation of an evaluation sample free of sulfated saccharides (dextrin, dextran 15000, xanthan gum, inulin, maltotriose, maltitol, sucrose, α-cyclodextrin (α-CD), mannitol, xylitol) at 37° C. for 7 days with the addition at any concentration, resulted in a decrease in the bFGF concentration of the medium to less than 10% of that of the 4° C. control. The 37° C. control also showed a decrease in the bFGF concentration of the medium to less than 10% of that of the 4° C. control. In contrast, evaluation samples containing sulfated saccharides showed a suppressive effect on a decrease in the bFGF concentration of the medium. Respective compounds showed the effect at the following concentrations: dextran sulfate (5000), not less than 250 pg/ml; dextran sulfate (25000), not less than 2.5 ng/ml; dextran sulfate (500,000), not less than 2.5 ng/ml; carageenan, not less than 2.5 µg/ml; cellulose SO$_3$Na, not less than 2.5 ng/ml; xanthan gum SO$_3$Na, not less than 25 ng/ml; fucoidan, not less than 2.5 ng/ml; alginate SO$_3$Na, not less than 2.5 ng/ml; inulin SO$_3$Na, not less than 2.5 ng/ml; maltoheptaose SO$_3$Na, 25 ng/ml and not less than 2.5 µg/ml; stachyose SO$_3$Na, not less than 250 ng/ml; maltotriose SO$_3$Na, not less than 2.5 µg/ml; maltitol SO$_3$Na, not less than 250 ng/ml; sucrose 8SO$_3$K, not less than 25 µg/ml; glucose SO$_3$Na, not less than 250 µg/ml; myo-inositol 6SO$_3$K, not less than 25 µg/ml; α-CD SO$_3$Na, not less than 250 ng/ml; mannitol SO$_3$Na, not less than 25 ng/ml; xylitol SO$_3$Na, not less than 250 µg/ml; erythritol SO$_3$Na, not less than 250 µg/ml; glycerol SO$_3$Na, not less than 2.5 mg/ml.

In addition, as shown in Table 8-2, evaluation samples containing maltotriose-hexamethylene diisocyanate-SO₃Na, dextran-hexamethylene diisocyanate-SO₃Na, gluconolactone-SO₃Na or tartrate-SO₃Na showed a suppressive effect on a decrease in the bFGF concentration of the medium. Respective compounds showed the effect at the following concentrations:

maltotriose-hexamethylene diisocyanate-SO₃Na, 2.5 ng/ml, 250 ng/ml to 2.5 mg/ml;

dextran-hexamethylene diisocyanate-SO₃Na, 25 ng/ml to 2.5 mg/ml;

gluconolactone-SO₃Na, 25 µg/ml, 2.5 mg/ml;

tartrate-SO₃Na, 250 ng/ml, 2.5 mg/ml.

Furthermore, as shown in Table 8-3, incubation of meso-erythritol SO₃Na, sucrose 8SO₃K and maltoheptaose SO₃Na at 37° C. for 3 days showed a suppressive effect on a decrease in the bFGF concentration in the medium, at a low concentration as compared to incubation for 7 days. Respective compounds showed the effect at the following concentrations:

meso-erythritol SO₃Na, not less than 25 µg/m;

sucrose 8SO₃K, not less than 250 ng/ml;

maltoheptaose SO₃Na, not less than 25 ng/ml.

2. Evaluation of bFGF Stabilization in Essential 8 Medium or ReproFF2 Medium

An influence of the addition of various test compounds at a concentration of 250 pg/ml to 2.5 mg/ml on the stabilization of bFGF in a medium prepared using an Essential 8 dedicated medium kit (A14666SA, Invitrogen) and according to the protocol (Essential 8 medium), or in ReproFF2 medium (ReproCELL Inc) prepared in the same manner, was evaluated. A test compound was dissolved in phosphate buffered saline, and diluted 10-fold with a serum-free medium to adjust the concentration shown in Table 4 (test sample). The test sample was left standing in a tightly sealed Falcon tube at 37° C. for 7 days, and the bFGF concentration was quantified by ELISA measurement. A phosphate buffered saline without a test compound was diluted 10-fold with Essential 8 medium or ReproFF2 medium, and left standing at 37° C. or 4° C. for 7 days, and used as a control.

TABLE 8-4

|  | pg | ng | | | µg | | | mg | |
| --- | --- | --- | --- | --- | --- | --- | --- | --- | --- |
|  | 250 | 2.5 | 25 | 250 | 2.5 | 25 | 250 | 2.5 | |
| dextran sulfate Na 5000 | x | x | − | +++ | +++ | +++ | +++ | +++ | |
| dextran sulfate Na (25000) | x | − | x | +++ | +++ | +++ | +++ | +++ | |
| dextran sulfate Na 500,000 | + | x | ++ | +++ | +++ | ++ | ++ | − | |
| dextran 15000 | x | x | x | x | x | x | x | ++ | Comp. Ex. |
| dextran-hexamethylene diisocyanate-SO3Na | x | x | x | +++ | +++ | +++ | +++ | ++ | |
| carageenan | x | x | x | − | − | ++ | ++ | − | |
| cellulose SO3Na | x | x | +++ | +++ | +++ | +++ | ++ | ++ | |
| xanthan gum SO3Na | x | x | x | +++ | +++ | +++ | ++ | x | |
| fucoidan | x | x | − | +++ | +++ | +++ | +++ | ++ | |
| alginate SO3Na | x | x | x | +++ | +++ | +++ | +++ | +++ | |
| chondroitin sulfate Na | x | x | x | x | x | x | + | +++ | |
| pectin SO3Na | x | x | x | +++ | +++ | +++ | +++ | ++ | |
| chitosan SO3Na | x | x | x | x | x | x | + | + | |

4° C. ctrl ratio
+++ not less than 70%,
++ not less than 50%,
+ not less than 30%,
− not less than 10%,
x less than 10%

TABLE 8-5

|  | pg | ng | | | µg | | | mg | |
| --- | --- | --- | --- | --- | --- | --- | --- | --- | --- |
|  | 250 | 2.5 | 25 | 250 | 2.5 | 25 | 250 | 2.5 | |
| maltoheptaose SO3Na | x | x | x | + | +++ | +++ | +++ | +++ | |
| α-CD SO3Na | x | x | x | x | + | +++ | +++ | +++ | |
| stachyose SO3Na | x | x | x | x | x | x | ++ | ++ | |
| maltotriose SO3Na | x | x | x | − | +++ | +++ | +++ | +++ | |
| maltotriose-hexamethylene diisocyanate-SO3Na | x | x | x | − | +++ | +++ | +++ | +++ | |
| maltotriose | x | x | x | x | x | x | x | x | Comp. Ex. |
| maltitol SO3Na | x | x | x | x | − | + | + | +++ | |
| sucrose 8SO3K | x | x | x | x | + | +++ | +++ | +++ | |
| glucose SO3Na | x | x | x | x | − | +++ | +++ | ++ | |
| mannitol SO3Na | x | x | x | x | − | +++ | +++ | +++ | |

TABLE 8-5-continued

|  | pg | ng | | µg | | | mg |
|---|---|---|---|---|---|---|---|
|  | 250 | 2.5 | 25 | 250 | 2.5 | 25 | 250 | 2.5 |
| erythritol SO3Na | x | x | x | x | x | + | +++ | +++ |
| myo-inositol 6SO3K | x | x | x | x | x | +++ | +++ | +++ |
| gluconolactone SO3Na | x | x | x | x | x | ++ | +++ | +++ |
| tartrate SO3Na | x | x | x | x | x | x | − | + |

4° C. ctrl ratio
+++ not less than 70%,
++ not less than 50%,
+ not less than 30%,
− not less than 10%,
x less than 10%

TABLE 8-6

|  | pg | ng | | µg | | | mg |
|---|---|---|---|---|---|---|---|
|  | 250 | 2.5 | 25 | 250 | 2.5 | 25 | 250 | 2.5 |
| dextran sulfate Na 5000 | − | − | − | − | ++ | +++ | +++ | +++ |
| dextran sulfate Na 25000 | − | − | − | − | +++ | +++ | +++ | +++ |
| dextran sulfate Na 500,000 | x | − | − | +++ | ++ | ++ | +++ | +++ |
| carageenan | x | − | − | − | − | + | +++ | +++ |
| chondroitin sulfate Na | − | − | x | − | x | − | + | +++ |
| sucrose SO3K | − | − | +++ | +++ | +++ | ++ | +++ | +++ |
| polyethylene sulfonate Na | x | − | x | − | +++ | +++ | +++ | +++ |

4° C. ctrl ratio
+++ not less than 70%,
++ not less than 50%,
+ not less than 30%,
− not less than 10%,
x less than 10%

The results obtained using Essential 8 medium are shown in Tables 8-4 and 8-5. Incubation of an evaluation sample free of a sulfated substance (dextran 15000 and maltotriose) at 37° C. for 7 days with the addition of a test compound at a concentration of not less than 250 µg/m resulted in a decrease in the bFGF concentration of the medium to less than 10% of that of the 4° C. control. The 37° C. control also showed a decrease in the bFGF concentration of the medium to less than 10% of that of the 4° C. control. In contrast, evaluation samples containing sulfated saccharide, maltotriose-hexamethylene diisocyanate-SO3Na, dextran-hexamethylene diisocyanate-SO3Na, gluconolactone-SO3Na or tartrate-SO3Na showed a suppressive effect on a decrease in the bFGF concentration of the medium. Respective compounds showed the effect at the following concentrations:

dextran sulfate Na (5000), not less than 25 ng/ml;
dextran sulfate Na (25000), 2.5 ng/ml, not less than 250 ng/ml;
dextran sulfate Na (500,000), 250 pg/ml, not less than 25 ng/ml;
dextran-hexamethylene diisocyanate-SO3Na, not less than 250 ng/ml;
carageenan, not less than 250 ng/ml;
cellulose SO3Na, not less than 25 ng/ml;
xanthan gum SO3Na, 250 ng/ml to 250 µg/ml;
fucoidan, not less than 25 ng/ml;
alginate SO3Na, not less than 250 ng/ml;
chondroitin sulfate Na, not less than 250 µg/ml;
pectin SO3Na, not less than 250 ng/ml;
chitosan SO3Na, not less than 250 µg/ml;
maltoheptaose SO3Na, not less than 250 ng/ml;
α-CD.SO3Na, not less than 2.5 µg/ml;
stachyose SO3Na, not less than 250 µg/ml;
maltotriose SO3Na, not less than 250 ng/ml;
maltotriose-hexamethylene diisocyanate-SO3Na, not less than 250 ng/ml;
maltitol SO3Na, not less than 2.5 µg/ml;
sucrose 8SO3K, not less than 2.5 µg/ml;
glucose SO3Na, not less than 2.5 µg/ml;
mannitol SO3Na, not less than 2.5 µg/ml;
erythritol SO3Na, not less than 25 µg/ml;
myo-inositol 6SO3K, not less than 25 µg/ml;
gluconolactone SO3Na, not less than 25 µg/ml;
tartrate SO3Na, not less than 250 µg/ml.

The results obtained using ReproFF2 medium are shown in Table 8-6. Evaluation samples containing dextran sulfate Na (5000) or dextran sulfate Na (25000) showed a suppressive effect on a decrease in the bFGF concentration of the medium. Respective compounds showed the effect at the following concentrations:

dextran sulfate Na (5000), not less than 250 pg/ml;
dextran sulfate Na (25000), not less than 250 pg/ml;
dextran sulfate Na (500,000), not less than 2.5 ng/ml;
carageenan, not less than 2.5 ng/ml;
chondroitin sulfate Na, 250 pg/ml to 2.5 ng/ml, 250 ng/ml, not less than 25 µg/ml;
sucrose SO3K, not less than 250 pg/ml;
polyethylene sulfonate Na, 2.5 ng/ml, not less than 250 ng/ml.

Example I-2. Evaluation in Cell Proliferation System

1. Evaluation of Mesenchymal Stem Cell Proliferation System (1) Cell Proliferation.

Human bone marrow-derived mesenchymal stem cells (Lonza, Human Mesenchymal Stem Cell) cultured in mesenchymal stem cell-dedicated medium (Lonza, MSCGM) or Dulbecco's Modified Eagle Medium (Invitrogen, GIBCO D-MEM) containing inactivated fetal bovine serum (Invitrogen, GIBCO FBS) and penicillin-streptomycin (Sigma-Aldrich Co. LLC.) were cultured in exchanged Lonza serum-free medium. The mesenchymal stem cells thus-acclimated to serum-free culture were suspended in Lonza serum-free medium, and seeded on a 24 well culture plate (Nippon Becton Dickinson Company, Ltd., Falcon culture plate) at 20,000 cells/well or a 6 well culture plate (Nippon Becton Dickinson Company, Ltd., Falcon culture plate) at 50,000 cells/well. Then, a test compound solution after filter sterilization and adjustment to a given concentration was added, and the cells were cultured in an incubator (Thermo Scientific, Forma incubator) under the 5% CO$_2$/37° C. conditions for 7 to 8 days. When the medium exchange was necessary, the medium was exchanged 2 to 3 days after the seeding. In this case, the test compound solution was also added again in the same manner as in seeding. In this case, various compound solutions were added again in the same manner as in seeding. After culturing for 7 to 8 days, the medium was removed and DNA quantification was performed. As a control, the cells were cultured in the same manner in a medium without a test compound and added with phosphate buffered saline.

(2) Calculation of Cell Number by DNA Quantification.

Sodium chloride (18.0 g) and trisodium citrate hydrate (8.83 g) were dissolved in pure water (100 ml), and this was further diluted 20-fold with pure water (sodium chloride-sodium citrate buffer). Sodium lauryl sulfate (50.4 mg) was dissolved in sodium chloride-sodium citrate buffer (252 ml) to give a sodium lauryl sulfate solution.

The medium in the 24 well culture plate was removed, and the cells were washed with phosphate buffered saline. The sodium lauryl sulfate solution (500 µl/well) was added, and the mixture was left standing at 37° C. for 4 hours. The sodium lauryl sulfate solution (1.0 ml) was also added to a cell pellet with a known cell number, and the mixture was left standing at 37° C. for 4 hours. As for the cells in the 24 well culture plate, a part (50 µl) of the lysate was transferred to a 96 well black microplate. The solution used for treating the cell pellets was successively diluted with sodium lauryl sulfate solution and used as solutions for drawing an analytical curve. Also, a part (50 µl) of the solutions for drawing an analytical curve was each transferred to the 96 well black microplate. A DNA chromogenic solution obtained by diluting bisbenzimide H33258 (04907-91, Nacalai Tesque) 1,000-fold with sodium chloride-sodium citrate buffer was added by 100 µl/well to the samples. The fluorescence was measured by a microplate reader (excitation wavelength: 355 nm, measurement wavelength: 460 nm) within 5 minutes from the addition. The cell number of the 24 well cell culture plate was calculated from the analytical curve drawn (conversion formula). The evaluation criteria were as follows.

⊙: number of cells is not less than 120% of that of control
○: number of cells is not less than 100% and less than 120% of that of control
–: number of cells is not less than 50% and less than 100% of that of control
x: number of cells is less than 50% of that of control

TABLE 9

Evaluation results of number of cells.

| | vs control (suppression of decrease in cell proliferation) | | | | | | | | |
|---|---|---|---|---|---|---|---|---|---|
| | pg | | ng | | | | µg | | |
| | 25 | 250 | 2.5 | 25 | 100 | 250 | 2.5 | 25 | 250 |
| fukoidan | | | | ○ | | ⊙ | X | | |
| dextran SO3Na (500,000) | ⊙ | ⊙ | ⊙ | ⊙ | | ○ | X | | |
| dextran SO3Na (25000) | ⊙ | ⊙ | ⊙ | ⊙ | | ⊙ | X | X | X |
| alginate SO3Na | | | | – | | ○ | ○ | X | X |
| inulin SO3Na | | | | – | | ○ | X | X | X |
| cellulose SO3Na | – | ○ | ○ | ○ | | ○ | ○ | | |
| xanthan gum SO3Na | ○ | – | – | ○ | | – | X | | |
| maltoheptaose SO3Na | ○ | ⊙ | ○ | – | | ○ | – | | |

TABLE 9-continued

Evaluation results of number of cells.

| | vs control (suppression of decrease in cell proliferation) | | | | | | | | |
|---|---|---|---|---|---|---|---|---|---|
| | pg | | ng | | | | µg | | |
| | 25 | 250 | 2.5 | 25 | 100 | 250 | 2.5 | 25 | 250 |
| dextran SO3Na (5000) | ⊙ | ⊙ | ⊙ | ⊙ | | ○ | ⊙ | – | |
| maltotriose SO3Na | ⊙ | ⊙ | ○ | ○ | | | ⊙ | ⊙ | |
| sucrose 8SO3K | ⊙ | ⊙ | ⊙ | ⊙ | | ○ | ⊙ | | |
| maltitol SO3Na | – | – | – | ○ | | – | ⊙ | | |
| mannitol SO3Na | | | | | ○ | – | ○ | ○ | – |
| xylitol SO3Na | ○ | ○ | ○ | ○ | | | ○ | ○ | |
| meso-erythritol SO3Na | ○ | ○ | – | ○ | | | ○ | – | |
| dextran-hexamethylene diisocyanate-SO3Na | ○ | ○ | – | ○ | | | – | X | |
| maltotriose-hexamethylene diisocyanate-SO3Na | ○ | ○ | – | – | | | ⊙ | – | |
| gluconolactone-SO3Na | ○ | ○ | – | – | | | – | – | |
| tartrate-SO3Na | – | – | ○ | – | | | – | – | | not less than 120%: ⊙,
not less than 100%: ○,
100%-50%: –,
less than 50: X

As shown in Table 9, the medium added with sulfated saccharide showed promoted cell proliferation as compared to the control (⊙ and ○ in Table 9). Respective compounds showed the effect at the following concentrations:
dextran sulfate (5000), 25 pg/ml to 2.5 µg/ml;
dextran sulfate (25000), 25 pg/ml to 250 ng/ml;
dextran sulfate (500,000), 25 pg/ml to 250 ng/ml;
sucrose 8SO$_3$K, 25 pg/ml to 2.5 µg/ml;
fucoidan, 25 ng/ml to 250 ng/ml;
alginiate SO$_3$Na (10,000-600,000), 250 ng/ml to 2.5 µg/ml;
mannitol SO$_3$Na, 100 ng/ml, 2.5 µg/ml to 25 µg/ml;
cellulose SO$_3$Na, 250 pg/ml to 2.5 µg/ml;
xanthan gum SO$_3$Na, 25 pg/ml, 25 ng/ml;
maltoheptaose SO$_3$Na, 25 pg/ml to 2.5 ng/ml, 250 ng/ml;
xylitol SO$_3$Na, 25 pg/ml to 2.5 µg/ml;
meso-erythritol SO$_3$Na, 25 pg/ml to 250 pg/ml, 25 ng/ml to 250 ng/ml;
maltotriose SO$_3$Na, 25 pg/ml to 2.5 µg/ml;
maltitol SO$_3$Na, 25 ng/ml, 2.5 µg/ml.

In addition, the medium added with maltotriose-hexamethylene diisocyanate-SO$_3$Na, dextran-hexamethylene diisocyanate-SO$_3$Na, gluconolactone-SO$_3$Na or tartrate-SO$_3$Na also showed promoted cell proliferation as compared to the control. Respective compounds showed the effect at the following concentrations:
dextran-hexamethylene diisocyanate-SO$_3$Na, 25 pg/ml to 250 pg/ml, 25 ng/ml;
maltotriose-hexamethylene diisocyanate-SO$_3$Na, 25 pg/ml to 250 pg/ml, 250 ng/ml;
gluconolactone-SO$_3$Na, 25 pg/ml to 250 pg/ml;
tartrate-SO$_3$Na, 2.5 ng/ml.

2. Evaluation in iPS Cell Proliferation System

The cell proliferation effect of various test compounds was evaluated using artificial pluripotent stem cell (iPS cell).

201B7 strain purchased from iPS Academia Japan, Inc. was grown in a culture container coated with a basal lamina matrix (matrigel manufactured by Nippon Becton Dickinson Company, Ltd., or a fragment containing an active domain of laminin 511 purchased from OSAKA UNIVERSITY) (Becton, Dickinson and Company, Falcon culture petri dish or Falcon culture plate), contained in a feeder-free medium for human ES/iPS cell (ReproCELL Inc, ReproFF2).

In this medium were suspended iPS cells in colony state, and a 2.5- to 3.5-fold diluted amount of the original culture was plated on a 6-well culture plate coated with a basal lamina matrix (Nippon Becton Dickinson Company, Ltd., Falcon culture plate). Then, a test compound solution after filter sterilization and adjustment to a given concentration was added, and the cells were cultured in an incubator (Thermo Scientific, Forma incubator) under the 5% $CO_2$/37° C. conditions for 6 to 12 days. When the medium exchange was necessary, the medium was exchanged every 2 or 3 days. In this case, the test compound solution was also added again in the same manner as in seeding. After culturing for 6 to 12 days, the medium was removed, the cells were detached from the culture plate by a trypsin-EDTA (Sigma-Aldrich Ltd.) or TrypLE Select (Invitrogen) treatment and the cell number was measured. The cell number was measured by the method described in "*Kaitei Saibou baiyou Nyuumon Note*, page 77-83, 2010, YODOSHA CO., LTD." which is incorporated herein by reference in its entirety. As a control, culture was similarly performed in a medium without a test compound and added with phosphate buffered saline.

When the cells were seeded in a dissociation state of the cells (single cell state), a test compound solution after filter sterilization was added to a medium containing Y-27632 (Nacalai Tesque) to a given concentration, and dispensed to a 6 well culture plate. Thereto were plated iPS cells suspended in a medium containing Y-27632 at 100,000 cells/well, and cultured for 6 to 8 days. On the next day of seeding, the medium was exchanged to a medium (without Y-27632) added with the test compound alone. When medium exchange was necessary, the medium was exchanged every 2 or 3 days. In this case, the test compound solution was also added again in the same manner as in seeding. After culturing for 6 to 8 days, the cell number was measured by a method similar to that mentioned above.

When the evaluation was performed in Essential 8 medium (Invitrogen), which is a different feeder-free medium for iPS cell, iPS cells cultured in a medium obtained by adding human serum albumin (Sigma-Aldrich Co. LLC) to Essential 8 medium were used.

The evaluation criteria were as follows:
⊙: number of cells is not less than 120% of that of control
○: number of cells is not less than 100% and less than 120% of that of control
–: number of cells is not less than 50% and less than 100% of that of control
x: number of cells is less than 50% of that of control
(blank: not evaluated)

TABLE 10-1

| test compound | kind of basal lamina matrix used for coating | kind of medium | ng | | | | |
|---|---|---|---|---|---|---|---|
| | | | 5 | 10 | 50 | 100 | 250 |
| dextran sulfate Na 5000 | matrigel | ReproFF2 medium | | ○ | ⊙ | – | |

TABLE 10-1-continued

| test compound | kind of basal lamina matrix used for coating | kind of medium | ng | | | | |
|---|---|---|---|---|---|---|---|
| | | | 5 | 10 | 50 | 100 | 250 |
| dextran sulfate Na 5000 | matrigel | Essential-8 medium | ⊙ | ⊙ | ⊙ | ⊙ | |
| dextran sulfate Na 5000 | laminin511 fragment | Essential-8 medium | | | ○ | | | not less than 120%: ⊙,
not less than 100%: ○,
100%-50%: –,
less than 50: X

TABLE 10-2

| test compound | kind of basal lamina matrix used for coating | kind of medium | ng | | |
|---|---|---|---|---|---|
| | | | 2.5 | 25 | 250 |
| dextran sulfate Na 25000 | matrigel | Essential-8 medium | ○ | – | X |
| dextran-hexamethylene diisocyanate-SO3Na | matrigel | Essential-8 medium | ○ | ○ | X |
| fucoidan | matrigel | Essential-8 medium | ⊙ | – | X |
| cellulose SO3Na | matrigel | Essential-8 medium | ○ | ○ | X |
| maltoheptaose SO3Na | matrigel | Essential-8 medium | ○ | ⊙ | – |
| maltotriose-hexamethylene diisocyanate-SO3Na | matrigel | Essential-8 medium | ⊙ | – | – |
| maltotriose SO3Na | matrigel | Essential-8 medium | – | ○ | ○ |
| sucrose 8SO3K | matrigel | Essential-8 medium | – | ○ | ○ |
| pectin SO3Na | matrigel | Essential-8 medium | – | ○ | ⊙ |
| xanthan gum SO3Na | matrigel | Essential-8 medium | ○ | ⊙ | ⊙ | not less than 120: ⊙,
not less than 100: ○,
100-50: –,
less than 50: X

As shown in Table 10-1, the medium added with dextran sulfate Na (5000) showed promoted cell proliferation as compared to the control (⊙ and ○ in Table 10-1). When the cells were cultured in ReproFF2 medium and using matrigel, cell proliferation was promoted at a concentration of 10 ng/ml to 50 ng/ml. When the cells were cultured in Essential 8 medium and using matrigel, cell proliferation was promoted at a concentration of 5 ng/ml to 250 ng/ml. When the cells were cultured in Essential 8 medium and using a fragment containing an active domain of laminin 511, cell proliferation was promoted at a concentration of 50 ng/ml. As shown in Table 10-2, superior iPS cell growth promoting activity was also confirmed when other sulfated saccharide was added to the medium.

Therefore, it was shown that the growth of iPS cell can be promoted by adding sulfated saccharide to the medium, irrespective of the kind of the medium and basal lamina matrix to be used.

Example I-3. Measurement of Content Level of Sulfur in Test Compound

The relationship between the content level of sulfur in a test compound (sulfur content) and the cell proliferation promoting effect was examined. The sulfur content was measured using ICPS-8100 manufactured by SHIMADZU CORPORATION and analyzed using ICPS-8000 series Ver1.03. As the reference standard of sulfur, the standard for ICP-MS manufactured by Accu Standard was used. Sulfur reference standard solutions (0, 1, 10, 30, 50 ppm) were prepared, and the sulfur content of the evaluation samples containing 0.01 wt % test compound was measured by an analytical curve method.

TABLE 11

|  | sulfur content Found (inorganic analysis) | effectiveness ELISA | cells |
|---|---|---|---|
| dextran SO3Na(5000) | 15 | +++ | ⊙ |
| dextran SO3Na(25000) | 13 | +++ | ⊙ |
| dextran SO3Na(500,000) | 13 | ++ | ⊙ |
| carageenan | 5 | + | not evaluated |
| cellulose SO3Na | 18 | ++ | ○ |
| xanthan gum SO3Na | 6 | + | ○ |
| fucoidan | 7 | ++ | ⊙ |
| maltoheptaose SO3Na | 16 | +++ | ⊙ |
| α-cyclodextrin SO3Na | 14 | ++ | not evaluated |
| stachyose SO3Na | 18 | +++ | not evaluated |
| maltotriose SO3Na | 13 | +++ | ⊙ |
| maltitol SO3Na | 17 | +++ | ⊙ |
| sucrose 8SO3K | 17 | + | ⊙ |
| glucose SO3Na | 23 | + | not evaluated |
| mannitol SO3Na | 17 | ++ | ○ |
| xylitol SO3Na | 25 | +++ | ○ |
| erythritol SO3Na | 16 | + | ○ |
| glycerol SO3Na | 23 | + | not evaluated |
| myo-inositol 6SO3K | 19 | +++ | not evaluated |
| maltotriose-hexamethylene diisocyanate-SO3Na | 12 | ++ | ⊙ |
| dextran-hexamethylene diisocyanate-SO3Na | 14 | +++ | ○ |
| gluconolactone-SO3Na | 14 | ++ | ○ |
| tartrate-SO3Na | 15 | ++ | ○ |
| pectin SO3Na | 6 | − | not evaluated |
| chondroitin SO3Na | 5 | + | not evaluated |
| chitosan SO3Na | 3 | x | not evaluated | effectiveness in ELISA evaluation of mesenchymal stem cells,
+++ 70%<
++ 50%<
+ 30%<
− 10%<
X less than 10%
growth of mesenchymal stem cell, control ratio
⊙ not less than 120%,
○ not less than 100%,
− 100-50%,
X less than 50%

The results are shown in Table 11. It was shown that the sulfur content of the test compound that showed a cell proliferation promoting effect was not less than 5 wt %.

The above results show that the growth of stem cell is promoted by adding a trace amount of sulfated saccharide to a medium containing bFGF.

II. Evaluation of Sulfated Polymer

Synthetic Example 1. Synthesis of Polyvinyl Alcohol SO₃Na

Polyvinyl alcohol (200 mg, manufactured by Acros) was dissolved in dehydrated dimethylformamide (6 ml, manufactured by KANTO CHEMICAL CO., INC.), sulfur trioxide trimethylamine complex (600 mg, manufactured by Aldrich) was added, and the mixture was stirred at 70° C. overnight. The solvent was removed by decantation, acetone was added, and the mixture was stirred and filtered. The obtained solid was dissolved in pure water (2 ml), 30% aqueous sodium acetate solution (1.5 ml) was added, and the mixture was stirred at room temperature for 2 hours. Ethanol (12 ml) was added to the reaction mixture, and the precipitate was collected by filtration. The obtained solid was dissolved in pure water (5 ml), dialyzed overnight using Spectra/Por MWCO 6,000-8,000 and freeze-dried to give a white solid (425 mg).

Synthetic Example 2. Synthesis of Polyvinyl Amine SO₃Na

Polyvinyl amine hydrochloride (300 mg, manufactured by Polysciences, Inc) was dissolved in pure water (25 ml), and the mixture was adjusted pH 9.13 while adding 2N sodium hydroxide. Sulfur trioxide trimethylamine complex (2.1 g) was added, and the mixture was stirred overnight. The solvent of the obtained reaction mixture was removed by decantation, and stirred in 30% sodium acetate (20 ml) for 30 minutes. The reaction mixture was dissolved in pure water (20 ml), dialyzed overnight using Spectra/Por MWCO 6,000-8,000 and freeze-dried to give a white solid (450 mg).

Synthetic Example 3. Synthesis of Polyallylamine SO₃Na

Polyallylamine L (1.5 g, 20% aqueous solution, manufactured by NACALAI TESQUE, INC.) was dissolved in pure water (25 ml), and 2N sodium hydroxide (5.26 ml) was added. Sulfur trioxide trimethylamine complex (2.9 g) was added, and the mixture was stirred overnight. The obtained reaction mixture was concentrated, and stirred in 30% sodium acetate (10 ml) for 2 hours. The reaction mixture was dissolved in pure water (20 ml), dialyzed overnight using Spectra/Por MWCO 1,000 and freeze-dried to give a white solid (670 mg).

Synthetic Example 4. Synthesis of Polyethyleneimine SO₃Na

Polyethyleneimine (1.07 g, manufactured by Wako Pure Chemical Industries, Ltd.) was dissolved in dehydrated dimethylformamide (18 ml), sulfur trioxide trimethylamine complex (4.2 g) was added, and the mixture was stirred overnight. The solvent of the obtained reaction mixture was removed by decantation, slurry-washed with acetone, filtered and stirred in 30% sodium acetate (20 ml) for 30 minutes. The reaction mixture was dissolved in pure water (20 ml), dialyzed overnight using Spectra/Por MWCO 1,000 and freeze-dried to give a white solid (400 mg).

Synthetic Example 5. Synthesis of Branched-Polyglycerol SO₃Na

Under an argon stream, to trimethylolpropane (127 mg, manufactured by Tokyo Chemical Industry Co., Ltd.) was added a solution of potassium methoxide (23.8 mg, manufactured by KANTO CHEMICAL CO., INC.) in dehydrated methanol (0.095 ml, manufactured by KANTO CHEMICAL CO., INC.), and the mixture was stirred for 15 minutes. Excess solvent was removed under reduced pressure, and Glycidol (5.5 ml, manufactured by KANTO CHEMICAL CO., INC.) was added dropwise at 95° C. over 6 hours. The reaction mixture was stirred overnight, dissolved in methanol (40 ml), and the mixture was stirred for 30 minutes. After passing through DOWEX MONOSPHERE 650C, the mixture was dialyzed for three nights using Spectra/Por MWCO 1,000, concentrated and dried to give an oily substance (1.54 g). The obtained oily substance (300 mg) was dissolved in dehydrated dimethylformamide (6 ml), sulfur trioxide trimethylamine complex (1.0 g) was added, and the mixture was stirred overnight. The solvent of the obtained reaction mixture was removed by decantation and slurry-washed with acetone, and the mixture was stirred in 30% sodium acetate (20 ml) for 30 minutes. The reaction mixture was dissolved in pure water (20 ml), dialyzed overnight using Spectra/Por MWCO 1,000 and freeze-dried to give a white solid (284 mg).

Synthetic Example 6. Synthesis of α-L-Polylysine $SO_3Na$

L-Lys(Z)-NCA (1 g, production was committed to China-Suzhou Tianma) was stirred in dehydrated chloroform (20 ml, manufactured by KANTO CHEMICAL CO., INC.), a solution of triethylamine (0.047 ml, manufactured by KANTO CHEMICAL CO., INC.) in dehydrated chloroform (1 ml) was added at 0° C., and the mixture was stirred for 3 days. The reaction mixture was dissolved in trifluoroacetic acid (10 ml, manufactured by Junsei Chemical Co., Ltd.), hydrobromic acid/acetic acid solution (2 ml, 30%, manufactured by Tokyo Chemical Industry Co., Ltd.) was added, and the mixture was stirred overnight. Dehydrating ether (40 ml, manufactured by KANTO CHEMICAL CO., INC.) was added, and the precipitated solid was filtered, concentrated and dried to give a white solid (269 mg). The obtained solid was dissolved in pure water (25 ml), and 1N sodium hydroxide (1.29 ml) was added. Sulfur trioxide trimethylamine complex (360 mg) was added, and the mixture was stirred overnight. The obtained reaction mixture was concentrated, sodium acetate (212 mg) was added, and the mixture was stirred for 2 hours. The reaction mixture was dissolved in pure water (20 ml), dialyzed overnight using Spectra/Por MWCO 100-500 and freeze-dried to give a white solid (82 mg).

Synthetic Example 7. Synthesis of α-L-Poly Methyl Glutamate/α-L-5-Hydroxynorvaline (5-$SO_3Na$) (2/8) Copolymer) (in the Present Specification, Sometimes to be Abbreviated as polyGlu/α-5-OH-Norvaline $SO_3Na$)

γ-L-Methyl-Glu-NCA (10 g, manufactured by Chuo Kasei Co., Ltd.) was dissolved in dehydrated dichloroethane (50 ml, manufactured by KANTO CHEMICAL CO., INC.) under an argon stream, a solution of N,N-dimethyl-1,3-propanediamine (0.007 ml, manufactured by KANTO CHEMICAL CO., INC.) in dichloroethane (0.07 ml) was added at 0° C., and the mixture was stirred for 3 days to give a solution of γ-L-methyl-polyglutamic acid in dichloroethane. To a part (3 g) of the obtained reaction mixture was added dehydrated dichloroethane (9 ml) under an argon atmosphere, lithium borohydridetetrahydrofuran solution (0.7 ml, 3 mol/L, manufactured by KANTO CHEMICAL CO., INC.) was added dropwise, and the mixture was stirred overnight. Saturated aqueous ammonium chloride solution was added to the reaction mixture, the mixture was stirred for a while, and the reaction mixture was adjusted with 1N hydrochloric acid to pH 1. The reaction mixture was concentrated, slurry-washed with methanol/ether (25 ml/25 ml), filtered and washed with pure water and methanol to give a white solid (232 mg). The obtained solid (200 mg) was dissolved in dehydrated dimethylformamide (10 ml), sulfur trioxide trimethylamine complex (700 mg) was added, and the mixture was stirred at 70° C. overnight. To the obtained reaction mixture was added 30% sodium acetate (5 ml), and the mixture was stirred for 30 minutes. The reaction mixture was dissolved in pure water (20 ml), dialyzed overnight using Spectra/Por MWCO 1,000 and freeze-dried to give a white solid (130 mg).

Synthetic Example 8. Synthesis of α-L-Polyglutamic Acid-γ-Taurine

The γ-methyl-polyglutamic acid (250 mg) synthesized in Synthetic Example 7 was dissolved in dehydrated dimethylformamide (10 ml), O-(7-aza-1H-benzotriazol-1-yl)-N',N',N',N'-tetramethyluronium hexafluorophosphate (690 mg, manufactured by Watanabe Chemical Industries, Ltd.), 1-hydroxy-7-azabenzotriazole (247 mg, manufactured by Watanabe Chemical Industries, Ltd.), diisopropylethylamine (317 μl, manufactured by Tokyo Chemical Industry Co., Ltd.) and taurine (227 mg, manufactured by Wako Pure Chemical Industries, Ltd.) were added, and the mixture was stirred at room temperature overnight. After completion of the reaction, the mixture was dissolved in pure water (4.5 ml), and dialyzed using Spectra/Por MWCO 1,000. The obtained solution was further neutralized with acidic resin (manufactured by organo) and freeze-dried to give a white solid (90 mg).

Synthetic Example 9. Synthesis of L-Triserine $SO_3Na$

L-H-Ser-Ser-Ser-OH (300 mg, manufactured by Bachem) was dissolved in dehydrated dimethylformamide (10 ml), sulfur trioxide trimethylamine complex (897 mg) was added, and the mixture was stirred at 70° C. overnight. The reaction mixture was concentrated, adjusted with 2N sodium hydroxide solution to pH 9, and concentrated. The obtained solid was carried on gel filtration column (Bio-Gel β-2, manufactured by Bio-Rad, Richmond, Calif.), and eluted with 0.1M aqueous ammonium hydrogen carbonate solution. The eluate was freeze-dried to give a white solid (400 mg).

Synthetic Example 10. Synthesis of Branched-Polyglycerol-Monomethyltetraethyleneglycol-$SO_3Na$ Under an argon stream, tetraethyleneglycol monomethylether (15 g, manufactured by Tokyo Chemical Industry Co., Ltd.) was dissolved in dehydrated tetrahydrofuran (45 ml, manufactured by KANTO CHEMICAL CO., INC.), sodium hydride (1.88 g, manufactured by KANTO CHEMICAL CO., INC.) was added by small portions, and the mixture was stirred for 3 hours. Epichlorohydrin (31 g, manufactured by Tokyo Chemical Industry Co., Ltd.) was slowly added dropwise, and the mixture was stirred for two nights. The reaction mixture was filtered through celite, and washed with methylene chloride (200 ml). The filtrate was washed twice with water (200 ml), dried over magnesium sulfate, filtered and concentrated. The residue was purified by silica gel column purification using ethyl acetate, concentrated, and dried to give a colorless oil (4.5 g).

Under an argon stream, to trimethylolpropane (127 mg) was added a solution of potassium methoxide (23.8 mg) in dehydrated methanol (0.095 ml), and the mixture was stirred for 15 minutes. Excess solvent was removed under reduced pressure, and Glycidol (5.5 ml) was added dropwise at 95° C. over 6 hours. The reaction mixture was stirred overnight, synthesized glycidyl monomethyl tetraethyleneglycol (4.5 ml) was added dropwise at 95° C. over 6 hours, and the reaction mixture was further stirred overnight. The mixture was dissolved in methanol (40 ml), stirred for 30 minutes, passed through DOWEX MONOSPHERE 650C, dialyzed overnight using Spectra/Por MWCO 1,000, concentrated and dried a colorless transparent oily substance (4.68 g). The obtained oily substance (300 mg) was dissolved in dehydrated dimethylformamide (6 ml), sulfur trioxide trimethylamine complex (1 g) was added, and the mixture was stirred at 70° C. overnight. The solvent of the obtained reaction mixture was removed by decantation, and slurry-washed with acetone. 30% Sodium acetate (6 ml) and water (50 ml) were added, and the mixture was stirred for 30 minutes. The reaction mixture was concentrated, washed with ethanol, dialyzed overnight using Spectra/Por MWCO 1,000, and freeze-dried to give a white solid (280 mg).

Synthetic Example 11. Synthesis of Branched-Polyglycerol-2-Furfuryl-SO$_3$Na

Under an argon stream, to trimethylolpropane (127 mg) was added a solution of potassium methoxide (23.8 mg) in dehydrated methanol (0.095 ml) was added, and the mixture was stirred for 15 minutes. Excess solvent was removed under reduced pressure, and Glycidol (5.5 ml) was added dropwise at 95° C. over 6 hours. The reaction mixture was stirred overnight, glycidyl isopropylether (4.55 ml, manufactured by Tokyo Chemical Industry Co., Ltd.) was added dropwise at 95° C. for 6 hours, and the reaction mixture was further stirred overnight. The mixture was dissolved in methanol (40 ml), stirred for 30 minutes, passed through DOWEX MONOSPHERE 650C, dialyzed overnight using Spectra/Por MWCO 1,000, concentrated and dried to give a yellow transparent oily substance (4.58 g). The obtained oily substance (300 mg) was dissolved in dehydrated dimethylformamide (6 ml), sulfur trioxide trimethylamine complex (1 g) was added, and the mixture was stirred at 70° C. overnight. The solvent of the obtained reaction mixture was removed by decantation, and slurry-washed with acetone. 30% Sodium acetate (6 ml) and water (50 ml) were added, and the mixture was stirred for 30 minutes. The reaction mixture was concentrated, washed with ethanol, dialyzed overnight using Spectra/Por MWCO 1,000, and freeze-dried to give a white solid (266 mg).

Synthetic Example 12. Synthesis of Branched-Polyglycerol-Isopropyloxy-SO$_3$Na

Under an argon stream, to trimethylolpropane (127 mg) was added a solution of potassium methoxide (23.8 mg) in dehydrated methanol (0.095 ml), and the mixture was stirred for 15 minutes. Excess solvent was removed under reduced pressure, and Glycidol (5.5 ml) was added dropwise at 95° C. for 6 hours. The reaction mixture was stirred overnight, glycidyl furfurylether (5.46 ml, manufactured by Aldrich) was added dropwise at 95° C. over 6 hours, and the reaction mixture was further stirred overnight. The mixture was dissolved in methanol (40 ml), stirred for 30 minutes, passed through DOWEX MONOSPHERE 650C, dialyzed overnight using Spectra/Por MWCO 1,000, concentrated and dried to give a yellow transparent oily substance (931 mg). The obtained oily substance (300 mg) was dissolved in dehydrated dimethylformamide (6 ml), sulfur trioxide trimethylamine complex (1 g) was added, and the mixture was stirred at 70° C. overnight. The solvent of the obtained reaction mixture was removed by decantation, and slurry-washed with acetone. 30% Sodium acetate (6 ml) and water (50 ml) were added, and the mixture was stirred for 30 minutes. The reaction mixture was concentrated, washed with ethanol, dialyzed overnight using Spectra/Por MWCO 1,000, and freeze-dried to give a black-brown solid (272 mg).

Example II-1. Evaluation of bFGF Stabilization in Medium (1) Preparation of Sample for bFGF Stabilization Evaluation.

As regards the stabilization of bFGF in a medium prepared using a Lonza dedicated complete synthetic medium kit (00190632, TAKARA BIO INC.) and according to the protocol (Lonza serum-free medium), an influence of the addition of the test compounds described in Table 12 was evaluated. A test compound was dissolved in phosphate buffered saline, and diluted 10-fold with a serum-free medium to adjust to the concentrations shown in Table 13 (test sample). The test sample was left standing in a tightly sealed Falcon tube at 37° C. for 7 days, and the bFGF concentration was quantified by ELISA measurement. A phosphate buffered saline without a test compound was diluted 10-fold with a serum-free medium, and left standing at 37° C. or 4° C. for 7 days, and used as a control.

TABLE 12

Test compound and evaluation concentration.

| | | 25 pg/ml | 250 pg/ml | 2.5 ng/ml | 25 ng/ml | 250 ng/ml | 2.5 μg/ml | 25 μg/ml | 250 μg/ml | 2.5 mg/ml |
|---|---|---|---|---|---|---|---|---|---|---|
| polyvinyl alcohol SO3Na | Synthe. Ex. 1 | ○ | ○ | ○ | ○ | ○ | ○ | ○ | ○ | |
| polyvinyl amine SO3Na | Synthe. Ex. 2 | | | | ○ | ○ | ○ | ○ | ○ | ○ |
| polyallylamine SO3Na | Synthe. Ex. 3 | | ○ | ○ | ○ | ○ | ○ | ○ | | |
| polyethyleneimine SO3Na | Synthe. Ex. 4 | | ○ | ○ | ○ | ○ | ○ | ○ | ○ | ○ |
| polyethylene sulfonate Na | Aldrich | | | ○ | ○ | ○ | ○ | ○ | | |
| polyvinyl alcohol | ACROS | | ○ | ○ | ○ | ○ | ○ | | | |
| branched-polyglycerol SO3Na | Synthe. Ex. 5 | | ○ | ○ | ○ | ○ | ○ | ○ | ○ | ○ |
| polylysine SO3Na | Synthe. Ex. 6 | | ○ | ○ | ○ | ○ | ○ | ○ | ○ | ○ |

TABLE 12-continued

Test compound and evaluation concentration.

| | | 25 pg/ml | 250 pg/ml | 2.5 ng/ml | 25 ng/ml | 250 ng/ml | 2.5 µg/ml | 25 µg/ml | 250 µg/ml | 2.5 mg/ml |
|---|---|---|---|---|---|---|---|---|---|---|
| α-poly methyl glutamate/α-5-hydroxynorvaline (5-SO3Na) (2/8) copolymer) | Synthe. Ex. 7 | | | | | | ○ | ○ | ○ | |
| α-polyglutamic acid-γ-taurine | Synthe. Ex. 8 | | | | ○ | ○ | ○ | ○ | ○ | ○ |
| triserine SO3Na | Synthe. Ex. 9 | | ○ | ○ | ○ | ○ | ○ | ○ | ○ | ○ |
| serine SO3Na | Watanabe Chemical Industries, Ltd. | | ○ | ○ | ○ | ○ | ○ | ○ | ○ | ○ |
| serine | Junsei Chemical Co., Ltd. | | ○ | ○ | ○ | ○ | ○ | ○ | ○ | ○ |
| branched-polyglycerol-methoxytetraethyleneglycol-SO3Na | Synthe. Ex. 10 | | ○ | ○ | ○ | ○ | ○ | ○ | ○ | ○ |
| branched-polyglycerol-isopropyl-SO3Na | Synthe. Ex. 11 | | ○ | ○ | ○ | ○ | ○ | ○ | ○ | ○ |
| branched-polyglycerol-2-furfuryl-SO3Na | Synthe. Ex. 12 | | ○ | ○ | ○ | ○ | ○ | ○ | ○ | ○ |

(2) Quantification of bFGF in Medium (ELISA Measurement).

A commercially available measurement kit (human bFGF ELISA kit, ELH-bFGF-001, Ray Biotech) was used for quantification of bFGF in the medium. The measurement procedures followed the protocol attached to the kit. The bFGF concentration of the serum-free medium was calculated from the analytical curve (conversion formula) drawn from the absorbance of an analytical curve standard solution. The evaluation criteria of Table 13 are as follows:

+++: bFGF concentration was not less than 70% relative to that of 4° C. control

++: bFGF concentration was not less than 50% and less than 70% relative to that of 4° C. control +: bFGF concentration was not less than 30% and less than 50% relative to that of 4° C. control −: bFGF concentration was not less than 10% and less than 30% relative to that of 4° C. control x: bFGF concentration was less than 10% relative to that of 4° C. control As shown in Table 13, incubation of an evaluation sample free of a sulfated polymer (polyvinyl alcohol) at 37° C. for 7 days with the addition at any concentration resulted in a decrease in the bFGF concentration of the medium to less than 10% of that of the 4° C. control. The 37° C. control also showed a decrease in the bFGF concentration of the medium to less than 10% of that of the 4° C. control. In contrast, evaluation samples containing sulfated polymer showed a suppressive effect on a decrease in the bFGF concentration of the medium. Respective compounds showed the effect at the following concentrations:

polyvinyl alcohol SO$_3$Na, not less than 25 pg/ml;
polyvinyl amine SO$_3$Na, not less than 25 ng/ml;
polyallylamine SO$_3$Na, not less than 250 ng/ml;
polyethyleneimine SO$_3$Na, 250 pg/ml and not less than 2.5 mg/ml;
polyethylene sulfonate Na, not less than 25 ng/ml;
branched-polyglycerol SO$_3$Na, not less than 25 ng/ml;
polylysine SO$_3$Na, not less than 2.5 µg/ml;
α-poly methyl glutamate/α-5-hydroxynorvaline (5-SO$_3$Na) (2/8) copolymer, not less than 250 µg/ml;

TABLE 13

Results of ELISA.

| | pg | | ng | | | µg | | | mg | |
|---|---|---|---|---|---|---|---|---|---|---|
| | 25 | 250 | 2.5 | 25 | 250 | 2.5 | 25 | 250 | 2.5 | 25 |
| polyvinyl alcohol SO3Na | + | − | + | ++ | ++ | +++ | + | − | | |
| polyvinyl amine SO3Na | | | | x | + | +++ | +++ | +++ | ++ | |
| polyallylamine SO3Na | | | | x | +++ | + | ++ | ++ | + | |
| polyethyleneimine SO3Na | | − | x | x | x | x | x | x | ++ | |
| polyethylene sulfonate Na | | x | x | − | ++ | ++ | ++ | ++ | | |
| polyvinyl alcohol | | x | x | x | x | x | x | | Comp. Ex. | |
| branched-polyglycerol SO3Na | | x | x | + | + | ++ | +++ | +++ | ++ | |
| polylysine SO3Na | | x | x | x | x | + | + | − | + | |
| α-poly methyl glutamate/α-5-hydroxynorvaline (5-SO3Na) (8/2) copolymer | | | | | | x | x | + | | |
| α-PGA-γ-taurine | | | x | x | x | | − | − | + | |
| triserine SO3Na | | x | x | x | x | x | − | ++ | ++ | |
| serine SO3Na | | x | x | x | x | x | − | +++ | ++ | |
| serine | | x | x | x | x | x | x | x | Comp. Ex. | |
| branched-polyglycerol | | x | x | x | x | − | ++ | ++ | Comp. Ex. | |

α-polyglutamic acid-γ-taurine, not less than 25 μg/ml;
triserine SO$_3$Na, not less than 25 μg/ml;
serine SO$_3$Na, not less than 25 μg/ml.

2. Evaluation of bFGF Stabilization in Essential 8 Medium or ReproFF2 Medium An influence of the addition of various test compounds at a concentration of 250 pg/ml to 2.5 mg/ml on the stabilization of bFGF in a medium prepared using an Essential 8 dedicated medium kit (A14666SA, Invitrogen) and according to the protocol (Essential 8 medium), or in ReproFF2 medium (ReproCELL Inc) prepared in the same manner, was evaluated. A test compound was dissolved in phosphate buffered saline, and diluted 10-fold with a serum-free medium to adjust the concentration shown in Table 12 (test sample). The test sample was left standing in a tightly sealed Falcon tube at 37° C. for 7 days, and the bFGF concentration was quantified by ELISA measurement. A phosphate buffered saline without a test compound was diluted 10-fold with Essential 8 medium or ReproFF2 medium, and left standing at 37° C. or 4° C. for 7 days, and used as a control.

The results obtained using Essential 8 medium are shown in Table 14-1. Respective compounds showed a suppressive effect on a decrease in the bFGF concentration of the medium at the following concentrations:

polyvinyl alcohol SO$_3$Na, not less than 25 ng/ml;
polyvinyl amine SO$_3$Na, not less than 250 ng/ml;
polyallylamine SO$_3$Na, not less than 250 ng/ml;
polyethyleneimine SO$_3$Na, not less than 2.5 mg/ml;
polyethylene sulfonate Na, not less than 250 ng/ml;
branched-polyglycerol SO$_3$Na, not less than 250 ng/ml;
branched-polyglycerol-2-furfuryl-SO$_3$Na, not less than 25 ng/ml;
branched-polyglycerol-methoxytetraethyleneglycol-SO$_3$Na, not less than 250 ng/ml;
polylysine SO$_3$Na, not less than 25 μg/ml;
α-poly methyl glutamate/α-5-hydroxynorvaline (5-SO$_3$Na,) (2/8) copolymer, not less than 25 μg/ml;
triserine SO$_3$Na, not less than 25 μg/ml.

The results obtained using ReproFF2 medium are shown in Table 14-2.

TABLE 14-1

| test compound | pg 250 | ng 2.5 | ng 25 | ng 250 | μg 2.5 | μg 25 | μg 250 | mg 2.5 | |
|---|---|---|---|---|---|---|---|---|---|
| polyvinyl alcohol SO3Na | x | x | +++ | +++ | +++ | +++ | +++ | +++ | |
| polyvinyl amine SO3Na | x | x | + | +++ | +++ | +++ | +++ | +++ | |
| polyallylamine SO3Na | x | x | + | +++ | +++ | +++ | +++ | +++ | |
| polyethyleneimine SO3Na | x | x | x | x | x | x | + | +++ | |
| polyethylene sulfonate Na | x | x | x | ++ | +++ | +++ | +++ | +++ | |
| branched-polyglycerol SO3Na | x | x | x | + | +++ | +++ | +++ | +++ | |
| branched-polyglycerol-2-furfuryl-SO3Na | x | − | ++ | +++ | +++ | ++ | + | x | |
| branched-polyglycerol-methoxytetraethyleneglycol-SO3Na | x | x | x | + | +++ | +++ | +++ | + | |
| polylysine SO3Na | x | x | x | x | x | ++ | +++ | +++ | |
| α-polyglutamic acid/α-5-hydroxynorvaline (5-SO3Na) (8/2) copolymer | x | x | x | x | − | +++ | +++ | +++ | |
| α-polyglutamic acid-γ-taurine | x | x | x | x | x | x | − | + | |
| triserine SO3Na | x | x | x | x | − | ++ | +++ | +++ | |
| polyphosphoric acid | x | x | x | x | x | x | x | +++ | Comp. Ex. |
| polyacrylic acid | x | x | x | x | x | x | +++ | +++ | Comp. Ex. |

4° C. ctrl ratio
+++ not less than 70%,
++ not less than 50%,
+ not less than 30%,
− not less than 10%,
x less than 10%

TABLE 14-2

| test compound | pg 250 | ng 2.5 | ng 25 | ng 250 | μg 2.5 | μg 25 | μg 250 | mg 2.5 |
|---|---|---|---|---|---|---|---|---|
| polyethylene sulfonate Na | x | − | x | − | +++ | +++ | +++ | +++ |

Addition of polyethylene sulfonate Na at not less than 2.5 μg/ml showed a suppressive effect on a decrease in the bFGF concentration of the medium.

Example II-2. Evaluation in Cell Proliferation System

1. Evaluation in Mesenchymal Stem Cell Proliferation System

The evaluation was performed in the same manner as in the above-mentioned Example I-1, 1. The results are shown in Table 15.

TABLE 15

Evaluation results of number of cells.

| | relative to control | | | | | | |
|---|---|---|---|---|---|---|---|
| | pg | | ng | | | | μg |
| test compound | 25 | 250 | 2.5 | 25 | 100 | 250 | 2.5 |
| polyvinyl alcohol SO3Na | | ○ | ○ | ○ | ⊙ | – | X |
| polyvinyl amine SO3Na | | – | – | ○ | | ○ | X |
| polyallylamine SO3Na | ○ | ○ | – | ○ | | – | X |
| polyethylene sulfonate Na | | | | ⊙ | | ○ | X |
| α-poly methyl glutamate/α-5-hydroxynorvaline (5-SO3Na) (2/8) copolymer | ○ | ○ | – | ○ | | ○ | ○ |
| α-polyglutamic acid-γ-taurine | ○ | ○ | – | ○ | | ○ | ○ |
| triserine SO3Na | – | ○ | ⊙ | – | | – | – |
| serine SO3Na | – | – | – | – | | – | – |
| branched-polyglycerol SO3Na | ○ | ○ | ○ | ○ | | ○ | – |
| branched-polyglycerol | – | – | – | – | | ○ | ○ |
| branched-polyglycerol-monomethyl-tetraethyleneglycol-SO3Na | ○ | ○ | ○ | – | | – | – |
| branched-polyglycerol-isopropyloxy-SO3Na | ○ | ○ | ○ | ○ | | – | – |
| polyphosphoric acid | – | – | – | – | | – | Comp. Ex. |
| sodium polyacrylate | – | – | – | – | | – | Comp. Ex. |

⊙ not less than 120,
○ not less than 100,
–: 100-50, less than 50: X

As shown in Table 15, medium added with a sulfated polymer promoted cell proliferation as compared to the control (⊙ and ○ in Table 15). Respective compounds showed the effect at the following concentrations:
polyvinyl alcohol SO₃Na, 250 pg/ml to 100 ng/ml;
polyvinyl amine SO₃Na, 25 ng/ml to 250 ng/ml;
polyallylamine SO₃Na, 25 pg/ml to 250 pg/ml, 25 ng/ml;
polyethylene sulfonate Na, 25 ng/ml to 250 ng/ml;
α-poly methyl glutamate/α-5-hydroxynorvaline (5-SO₃Na) (2/8) copolymer), 25 pg/ml to 250 pg/ml, 25 ng/ml to 2.5 μg/ml;
α-glutamic acid-γ-taurine, 25 pg/ml, 25 ng/ml to 2.5 μg/ml;
triserine SO₃Na, 250 pg/ml to 2.5 ng/ml;
branched-polyglycerol SO₃Na, 25 pg/ml to 25 ng/ml, 250 ng/ml;
branched-polyglycerol-monomethyltetraethyleneglycol-SO₃Na, 25 pg/ml to 2.5 ng/ml;
branched-polyglycerol-isopropyloxy-SO₃Na, 25 pg/ml to 25 ng/ml.

2. Evaluation in iPS Cell Proliferation System

The evaluation was performed in the same manner as in the above-mentioned I-2, 2. The results are shown in Table 16.

TABLE 16

| | kind of basal lamina matrix used for coating | kind of medium | ng | | |
|---|---|---|---|---|---|
| test compound | | | 2.5 | 25 | 250 |
| polyethylene sulfonate Na | matrigel | Essential-8 medium | ○ | ⊙ | ⊙ |
| branched-polyglycerol SO3Na | matrigel | Essential-8 medium | ○ | ⊙ | – |
| polyvinyl alcohol SO3Na | matrigel | Essential-8 medium | ○ | ⊙ | X |
| polyvinyl amine SO3Na | matrigel | Essential-8 medium | – | ○ | – |
| polyGlu/α-5-OH-norvaline SO3Na | matrigel | Essential-8 medium | – | ○ | ○ |
| polyallylamine SO3Na | matrigel | Essential-8 medium | ○ | ⊙ | X | not less than 120: ⊙,
not less than 100: ○,
100-50: –,
less than 50: X

As shown in Table 16, the media added with various sulfated polymers promoted cell proliferation as compared to the control (⊙ and ○ in Table 16).
The above results show that the growth of stem cell is promoted by adding a trace amount of sulfated polymer to a medium containing bFGF.

Example II-3. Measurement of the Content Level of Sulfur in Test Compound

The measurement was performed in the same manner as in the above-mentioned I-3. The results are shown in Table 17.

TABLE 17

| | | sulfur content Found (inorganic analysis) | effectiveness | |
|---|---|---|---|---|
| | | | ELISA | cells |
| polyvinyl alcohol SO3Na | Synthe. Ex. 1 | 15 | +++ | ⊙ |
| polyvinyl amine SO3Na | Synthe. Ex. 2 | 15 | +++ | ○ |
| polyallylamine SO3Na | Synthe. Ex. 3 | 15 | +++ | ○ |
| polyethyleneimine SO3Na | Synthe. Ex. 4 | 16 | ++ | not evaluated |
| branched-polyglycerol SO3Na | Synthe. Ex. 5 | 15 | +++ | ○ |
| polylysine SO3Na | Synthe. Ex. 6 | 11 | + | not evaluated |
| α-polyglutamic acid/α-hydroxy-norvaline (5-SO3Na) (2/8) copolymer) | Synthe. Ex. 7 | 1 | + | ○ |
| α-polyglutamic acid-γ-taurine | Synthe. Ex. 8 | 12 | | ○ |
| triserine SO3Na | Synthe. Ex. 9 | 18 | ++ | ⊙ |

TABLE 17-continued

|  |  | sulfur content Found (inorganic analysis) | effectiveness | |
|---|---|---|---|---|
|  |  |  | ELISA | cells |
| serine SO3H | Watanabe Chemical Industries, Ltd. | 17.6 | +++ | − |
| branched-polyglycerol-monomethyltetraethyleneglycol-SO3Na | Synthe. Ex. 10 | 22 | ++ | ○ |
| branched-polyglycerol-isopropyloxy-SO3Na | Synthe. Ex. 11 | 19 | + | ○ |

INDUSTRIAL APPLICABILITY

According to the present invention, in the culture of stem cell using a medium containing FGF, the stem cell can be grown more efficiently than in the media used conventionally. According to the present invention, the frequency of medium exchange during culture can be reduced and the cost of stem cell culture can be decreased, which contribute to further promotion of the utilization of stem cells in medicine, research development and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for culturing a stem cell, comprising culturing the stem cell in a medium comprising:
    a fibroblast growth factor (FGF), and
    a sulfated compound or a pharmaceutically acceptable salt thereof,
    wherein said sulfated compound or a pharmaceutically acceptable salt thereof is present in said medium at a concentration that promotes the growth of said stem cell in the presence of FGF, and
    wherein said sulfated compound or a pharmaceutically acceptable salt thereof is a sulfated substance of a saccharide polymer crosslinked by a diisocyanate compound or a pharmaceutically acceptable salt thereof.

2. The method according to claim 1, wherein said sulfated substance of a saccharide polymer crosslinked by a diisocyanate compound or pharmaceutically acceptable salt thereof is maltotriose-hexamethylene diisocyanate-SO₃Na or dextran-hexamethylene diisocyanate-SO₃Na.

3. The method according to claim 1, wherein said FGF is a basic fibroblast growth factor (bFGF).

4. The method according to claim 1, wherein said stem cell is a mesenchymal stem cell, an embryonic stem cell or an artificial pluripotent stem cell.

5. A method for culturing a stem cell, comprising culturing the stem cell in a medium comprising:
    a fibroblast growth factor (FGF), and
    a sulfated compound or a pharmaceutically acceptable salt thereof,
    wherein said sulfated compound or a pharmaceutically acceptable salt thereof is present in said medium at a concentration that promotes the growth of said stem cell in the presence of FGF, and
    wherein said sulfated compound or pharmaceutically acceptable salt thereof is a sulfated substance of sugar-lactone or a pharmaceutically acceptable salt thereof.

6. The method according to claim 5, wherein said sulfated substance of sugar-lactone or pharmaceutically acceptable salt thereof is gluconolactone-SO₃Na.

7. The method according to claim 5, wherein said FGF is a basic fibroblast growth factor (bFGF).

8. The method according to claim 5, wherein said stem cell is a mesenchymal stem cell, an embryonic stem cell or an artificial pluripotent stem cell.

9. A method for culturing a stem cell, comprising culturing the stem cell in a medium comprising:
    a fibroblast growth factor (FGF), and
    a sulfated compound or a pharmaceutically acceptable salt thereof,
    wherein said sulfated compound or a pharmaceutically acceptable salt thereof is present in said medium at a concentration that promotes the growth of said stein cell in the presence of FGF, and
    wherein said sulfated compound or pharmaceutically acceptable salt thereof is a sulfated substance of tartrate-SO₃Na or a pharmaceutically acceptable salt thereof.

10. The method according to claim 9, wherein said FGF is a basic fibroblast growth factor (bFGF).

11. The method according to claim 9, wherein said stem cell is a mesenchymal stem cell, an embryonic stem cell or an artificial pluripotent stem cell.

* * * * *